United States Patent
Curtis et al.

(10) Patent No.: US 9,545,469 B2
(45) Date of Patent: *Jan. 17, 2017

(54) DIALYSIS SYSTEM WITH ULTRAFILTRATION CONTROL

(71) Applicant: OUTSET MEDICAL, INC., San Jose, CA (US)

(72) Inventors: James R. Curtis, Portland, OR (US); Ladislaus F. Nonn, Portland, OR (US); Julie Wrazel, Portland, OR (US)

(73) Assignee: OUTSET MEDICAL, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/225,712

(22) Filed: Aug. 1, 2016

(65) Prior Publication Data

US 2016/0339162 A1 Nov. 24, 2016

Related U.S. Application Data

(63) Continuation of application No. 14/305,952, filed on Jun. 16, 2014, which is a continuation of application
(Continued)

(51) Int. Cl.
*A61M 1/16* (2006.01)
*A61M 1/34* (2006.01)
*G05D 7/06* (2006.01)

(52) U.S. Cl.
CPC .............. *A61M 1/1647* (2014.02); *A61M 1/16* (2013.01); *A61M 1/1601* (2014.02); *A61M 1/165* (2014.02);
(Continued)

(58) Field of Classification Search
CPC .... A61M 1/16; A61M 1/1601; A61M 1/1645; A61M 1/1647; A61M 1/165; A61M 1/34; A61M 2205/12; A61M 2205/3334; A61M 2205/52; A61M 2205/70; A61M 2205/702; A61M 2205/3331; F04B 13/00; F04B 23/06; F04B 49/065; F04B 51/00; G05B 15/02; G05D 7/076

See application file for complete search history.

(56) References Cited

U.S. PATENT DOCUMENTS 3,356,360 A 12/1967 Ward
3,695,445 A 10/1972 Esmond
(Continued)

FOREIGN PATENT DOCUMENTS

CN 200951223 Y 9/2007
DE 8702995 U1 6/1987
(Continued)

OTHER PUBLICATIONS

Allis et al., "Chapter 16: Nanostructural Architectures from Molecular Building Blocks," in Handbook of Nanoscience, Engineering, and Technology, 1st Edition (Electrical Engineering Handbook), CRC Press LLC, Boca Raton, FL, Chapter 16 (70 pgs.), Oct. 2002.
(Continued)

*Primary Examiner* — John Kim
(74) *Attorney, Agent, or Firm* — Shay Glenn LLP

(57) ABSTRACT

Systems and methods are disclosed for performing hemodialysis that include fluid handling systems that provide accurate control over the type and level of hemodialysis being performed. The system includes a first pump for pumping dialysate into a dialyzer and a second pump for pumping dialysate out of the dialyzer. The system also includes a third pump that provides improved control of a level of ultrafiltration, hemodiafiltration, or both.

13 Claims, 6 Drawing Sheets

Related U.S. Application Data

No. 12/795,498, filed on Jun. 7, 2010, now Pat. No. 8,753,515.

(60) Provisional application No. 61/267,043, filed on Dec. 5, 2009.

(52) U.S. Cl.
CPC .............. *A61M 1/34* (2013.01); *G05D 7/0676* (2013.01); *A61M 2205/3331* (2013.01); *A61M 2205/3334* (2013.01); *A61M 2205/70* (2013.01); *A61M 2205/702* (2013.01)

(56) References Cited

U.S. PATENT DOCUMENTS

| | | |
|---|---|---|
| 3,710,237 A | 1/1973 | Watson et al. |
| 3,762,032 A | 10/1973 | Bowling et al. |
| 3,809,309 A | 5/1974 | Batista |
| 3,827,563 A | 8/1974 | Boe et al. |
| 3,965,008 A | 6/1976 | Dawson |
| 4,080,295 A | 3/1978 | Riede |
| 4,089,456 A | 5/1978 | Toppen et al. |
| 4,100,068 A | 7/1978 | Jordan et al. |
| 4,110,220 A | 8/1978 | Lavender |
| 4,115,273 A | 9/1978 | Winstead |
| 4,155,157 A | 5/1979 | Gersbacher |
| 4,172,033 A | 10/1979 | Willock |
| 4,194,014 A | 3/1980 | Hermans et al. |
| 4,204,628 A | 5/1980 | Houston et al. |
| 4,209,391 A | 6/1980 | Lipps |
| 4,229,299 A | 10/1980 | Savitz et al. |
| 4,231,366 A | 11/1980 | Schael |
| 4,267,040 A | 5/1981 | Schal |
| 4,293,409 A | 10/1981 | Riede et al. |
| 4,310,416 A | 1/1982 | Tanaka et al. |
| 4,317,725 A | 3/1982 | Kume et al. |
| 4,342,651 A | 8/1982 | Ahrens |
| 4,476,022 A | 10/1984 | Doll |
| 4,486,303 A | 12/1984 | Brous |
| 4,500,426 A | 2/1985 | Ishii et al. |
| 4,508,622 A | 4/1985 | Polaschegg |
| 4,536,201 A | 8/1985 | Brorsson et al. |
| 4,624,784 A | 11/1986 | Lefebvre |
| 4,647,748 A | 3/1987 | Glassman |
| 4,661,246 A | 4/1987 | Ash |
| 4,689,108 A | 8/1987 | Barry, Jr. et al. |
| 4,756,835 A | 7/1988 | Wilson |
| 4,769,134 A | 9/1988 | Allan et al. |
| 4,770,787 A | 9/1988 | Heath et al. |
| 4,773,991 A | 9/1988 | Aid |
| 4,786,411 A | 11/1988 | Benattar et al. |
| 4,827,430 A | 5/1989 | Aid et al. |
| 4,869,421 A | 9/1989 | Norris et al. |
| 4,875,619 A | 10/1989 | Anderson et al. |
| 4,889,635 A | 12/1989 | Chevallet |
| 4,894,164 A | 1/1990 | Polaschegg |
| 4,923,613 A | 5/1990 | Chevallet |
| 5,087,930 A | 2/1992 | Roy et al. |
| 5,092,836 A | 3/1992 | Polaschegg |
| 5,094,749 A | 3/1992 | Seita et al. |
| 5,147,605 A | 9/1992 | Tatsuno et al. |
| 5,227,049 A | 7/1993 | Chevallet et al. |
| 5,232,145 A | 8/1993 | Alley et al. |
| 5,236,476 A | 8/1993 | Klick |
| 5,247,434 A | 9/1993 | Peterson et al. |
| 5,259,961 A | 11/1993 | Eigendorf |
| 5,312,550 A | 5/1994 | Hester |
| 5,313,023 A | 5/1994 | Johnson |
| 5,316,676 A | 5/1994 | Drori |
| 5,326,476 A | 7/1994 | Grogan et al. |
| 5,342,326 A | 8/1994 | Peppel et al. |
| 5,344,392 A | 9/1994 | Senninger et al. |
| 5,346,472 A | 9/1994 | Keshaviah et al. |
| 5,360,395 A | 11/1994 | Utterberg |
| 5,385,623 A | 1/1995 | Diaz |
| 5,394,732 A | 3/1995 | Johnson et al. |
| 5,395,351 A | 3/1995 | Munsch |
| 5,401,238 A | 3/1995 | Pirazzoli |
| 5,409,612 A | 4/1995 | Maltais et al. |
| 5,421,208 A | 6/1995 | Packard et al. |
| 5,439,451 A | 8/1995 | Collinson et al. |
| 5,469,264 A | 11/1995 | Shigemori |
| 5,472,614 A | 12/1995 | Rossi |
| 5,489,385 A | 2/1996 | Raabe et al. |
| 5,498,253 A | 3/1996 | Aswad et al. |
| 5,498,338 A | 3/1996 | Kruger et al. |
| 5,503,624 A | 4/1996 | Roeher et al. |
| 5,520,640 A | 5/1996 | Utterberg |
| 5,526,357 A | 6/1996 | Jandrell |
| 5,533,996 A | 7/1996 | Murphey et al. |
| 5,534,328 A | 7/1996 | Ashmead et al. |
| 5,536,258 A | 7/1996 | Folden |
| 5,580,460 A | 12/1996 | Polaschegg |
| 5,580,523 A | 12/1996 | Bard |
| 5,582,600 A | 12/1996 | Loh |
| 5,591,016 A | 1/1997 | Kubota et al. |
| 5,591,344 A | 1/1997 | Kenley et al. |
| 5,593,581 A | 1/1997 | Lescoche |
| 5,595,712 A | 1/1997 | Harbster et al. |
| 5,609,770 A | 3/1997 | Zimmerman et al. |
| 5,610,645 A | 3/1997 | Moore et al. |
| 5,611,214 A | 3/1997 | Wegeng et al. |
| 5,613,663 A | 3/1997 | Schmidt et al. |
| 5,615,996 A | 4/1997 | Suzuki et al. |
| 5,618,268 A | 4/1997 | Raines et al. |
| 5,618,441 A | 4/1997 | Rosa et al. |
| 5,620,608 A | 4/1997 | Rosa et al. |
| 5,623,969 A | 4/1997 | Raines |
| 5,624,572 A | 4/1997 | Larson et al. |
| 5,629,871 A | 5/1997 | Love et al. |
| 5,630,804 A | 5/1997 | Imada et al. |
| 5,643,190 A | 7/1997 | Utterberg |
| 5,647,984 A | 7/1997 | Hovland et al. |
| 5,648,684 A | 7/1997 | Bertin et al. |
| 5,650,071 A | 7/1997 | Brugger et al. |
| 5,662,144 A | 9/1997 | Lo et al. |
| 5,685,835 A | 11/1997 | Brugger |
| 5,689,966 A | 11/1997 | Zess et al. |
| 5,693,008 A | 12/1997 | Brugger et al. |
| 5,698,916 A | 12/1997 | Eguchi |
| 5,711,883 A | 1/1998 | Folden et al. |
| 5,713,850 A | 2/1998 | Heilmann et al. |
| 5,725,773 A | 3/1998 | Polaschegg |
| 5,743,892 A | 4/1998 | Loh et al. |
| 5,744,031 A | 4/1998 | Bene |
| 5,749,226 A | 5/1998 | Bowman et al. |
| 5,769,985 A | 6/1998 | Kawakami et al. |
| 5,779,833 A | 7/1998 | Cawley et al. |
| 5,782,575 A | 7/1998 | Vincent et al. |
| 5,788,099 A | 8/1998 | Treu et al. |
| 5,788,851 A | 8/1998 | Kenley et al. |
| 5,792,367 A | 8/1998 | Mattisson et al. |
| 5,811,062 A | 9/1998 | Wegeng et al. |
| 5,813,235 A | 9/1998 | Peterson |
| 5,851,202 A | 12/1998 | Carlsson |
| 5,858,238 A | 1/1999 | Mcrea et al. |
| 5,858,239 A | 1/1999 | Kenley et al. |
| 5,861,555 A | 1/1999 | Hobro et al. |
| 5,868,930 A | 2/1999 | Kopf |
| 5,879,316 A | 3/1999 | Safar et al. |
| 5,881,774 A | 3/1999 | Utterberg |
| 5,885,456 A | 3/1999 | Charkoudian et al. |
| 5,895,368 A | 4/1999 | Utterberg |
| 5,903,211 A | 5/1999 | Flego et al. |
| 5,910,138 A | 6/1999 | Sperko et al. |
| 5,914,033 A | 6/1999 | Carlsson |
| 5,921,678 A | 7/1999 | Desai et al. |
| 5,928,177 A | 7/1999 | Brugger et al. |
| 5,928,180 A | 7/1999 | Krivitski et al. |
| 5,932,103 A | 8/1999 | Kenley et al. |
| 5,932,940 A | 8/1999 | Epstein et al. |
| 5,938,634 A | 8/1999 | Packard |
| 5,938,938 A | 8/1999 | Bosetto et al. |

(56) References Cited

U.S. PATENT DOCUMENTS

| | | |
|---|---|---|
| 5,951,870 A | 9/1999 | Utterberg |
| 5,957,898 A | 9/1999 | Jepson et al. |
| 5,974,867 A | 11/1999 | Forster et al. |
| 5,976,115 A | 11/1999 | Parris et al. |
| 5,983,947 A | 11/1999 | Utterberg |
| 5,984,903 A | 11/1999 | Nadal |
| 5,993,174 A | 11/1999 | Konishi |
| 6,003,556 A | 12/1999 | Brugger et al. |
| 6,010,623 A | 1/2000 | Schnell et al. |
| 6,024,276 A | 2/2000 | Hirata et al. |
| 6,032,926 A | 3/2000 | Fuchs |
| 6,036,680 A | 3/2000 | Horne et al. |
| 6,039,877 A | 3/2000 | Chevallet et al. |
| 6,041,801 A | 3/2000 | Gray et al. |
| 6,044,691 A | 4/2000 | Kenley et al. |
| 6,048,432 A | 4/2000 | Ecer |
| 6,058,934 A | 5/2000 | Sullivan |
| 6,064,797 A | 5/2000 | Crittendon et al. |
| 6,066,261 A | 5/2000 | Spickermann |
| 6,071,269 A | 6/2000 | Schnell et al. |
| 6,074,559 A | 6/2000 | Hahmann et al. |
| 6,077,443 A | 6/2000 | Goldau |
| 6,082,891 A | 7/2000 | Schubert et al. |
| 6,100,463 A | 8/2000 | Ladd et al. |
| 6,109,994 A | 8/2000 | Cho et al. |
| 6,113,785 A | 9/2000 | Miura et al. |
| 6,117,115 A | 9/2000 | Hill et al. |
| 6,117,123 A | 9/2000 | Barney et al. |
| 6,121,539 A | 9/2000 | Johnson et al. |
| 6,123,798 A | 9/2000 | Gandhi et al. |
| 6,126,723 A | 10/2000 | Drost et al. |
| 6,126,831 A | 10/2000 | Goldau et al. |
| 6,129,973 A | 10/2000 | Martin et al. |
| 6,132,616 A | 10/2000 | Twardowski et al. |
| 6,139,754 A | 10/2000 | Hartranft et al. |
| 6,142,008 A | 11/2000 | Cole et al. |
| 6,143,181 A | 11/2000 | Falkvall et al. |
| 6,143,247 A | 11/2000 | Sheppard et al. |
| 6,148,635 A | 11/2000 | Beebe et al. |
| 6,153,102 A | 11/2000 | Kenley et al. |
| 6,165,149 A | 12/2000 | Utterberg et al. |
| 6,165,161 A | 12/2000 | York et al. |
| 6,167,910 B1 | 1/2001 | Chow |
| 6,187,198 B1 | 2/2001 | Utterberg |
| 6,187,199 B1 | 2/2001 | Goldau |
| 6,192,596 B1 | 2/2001 | Bennett et al. |
| 6,193,462 B1 | 2/2001 | Kubota |
| 6,202,312 B1 | 3/2001 | Rando |
| 6,203,522 B1 | 3/2001 | Holmberg et al. |
| 6,203,535 B1 | 3/2001 | Barney et al. |
| 6,212,333 B1 | 4/2001 | Olk et al. |
| 6,220,299 B1 | 4/2001 | Arvidsson et al. |
| 6,221,040 B1 | 4/2001 | Kleinekofort |
| 6,221,064 B1 | 4/2001 | Nadal |
| 6,223,130 B1 | 4/2001 | Gray et al. |
| 6,225,497 B1 | 5/2001 | Becker et al. |
| 6,234,773 B1 | 5/2001 | Hill et al. |
| 6,251,279 B1 | 6/2001 | Peterson et al. |
| 6,254,567 B1 | 7/2001 | Treu et al. |
| 6,254,754 B1 | 7/2001 | Ross et al. |
| 6,258,276 B1 | 7/2001 | Mika et al. |
| 6,261,282 B1 | 7/2001 | Jepson et al. |
| 6,277,277 B1 | 8/2001 | Jacobi et al. |
| 6,280,406 B1 | 8/2001 | Dolecek et al. |
| 6,284,141 B1 | 9/2001 | Shaldon et al. |
| 6,302,653 B1 | 10/2001 | Bryant et al. |
| 6,308,721 B1 | 10/2001 | Bock et al. |
| 6,309,673 B1 | 10/2001 | Duponchelle et al. |
| 6,322,551 B1 | 11/2001 | Brugger |
| 6,323,662 B2 | 11/2001 | Ferri |
| 6,325,774 B1 | 12/2001 | Bene et al. |
| 6,329,139 B1 | 12/2001 | Nova et al. |
| 6,331,252 B1 | 12/2001 | El Sayyid et al. |
| 6,334,301 B1 | 1/2002 | Otsap et al. |
| 6,343,614 B1 | 2/2002 | Gray et al. |
| 6,344,033 B1 | 2/2002 | Jepson et al. |
| 6,346,084 B1 | 2/2002 | Schnell et al. |
| 6,347,711 B1 | 2/2002 | Goebel et al. |
| 6,349,170 B1 | 2/2002 | Fressinet et al. |
| 6,350,260 B1 | 2/2002 | Goebel et al. |
| 6,355,161 B1 | 3/2002 | Shah et al. |
| 6,357,332 B1 | 3/2002 | Vecchio |
| 6,365,041 B1 | 4/2002 | Hoadley |
| 6,368,505 B1 | 4/2002 | Grummert et al. |
| 6,375,871 B1 | 4/2002 | Bentsen et al. |
| 6,382,923 B1 | 5/2002 | Gray |
| 6,387,069 B1 | 5/2002 | Utterberg |
| 6,395,180 B2 | 5/2002 | Chioini et al. |
| 6,415,860 B1 | 7/2002 | Kelly et al. |
| 6,416,293 B1 | 7/2002 | Bouchard et al. |
| 6,423,022 B1 | 7/2002 | Roeher et al. |
| 6,432,309 B1 | 8/2002 | Fuke et al. |
| 6,454,736 B1 | 9/2002 | Ludt et al. |
| 6,454,942 B1 | 9/2002 | Shintani et al. |
| 6,468,056 B1 | 10/2002 | Murakoshi |
| 6,477,058 B1 | 11/2002 | Luebs et al. |
| 6,481,982 B1 | 11/2002 | Yokomichi |
| 6,485,263 B1 | 11/2002 | Bryant et al. |
| 6,488,842 B2 | 12/2002 | Nagaoka |
| 6,488,872 B1 | 12/2002 | Beebe et al. |
| 6,503,062 B1 | 1/2003 | Gray et al. |
| 6,514,225 B1 | 2/2003 | Utterberg et al. |
| 6,514,412 B1 | 2/2003 | Insley et al. |
| 6,526,357 B1 | 2/2003 | Soussan et al. |
| 6,527,728 B2 | 3/2003 | Zhang |
| 6,530,262 B1 | 3/2003 | Esser |
| 6,536,742 B2 | 3/2003 | Lotz et al. |
| 6,537,506 B1 | 3/2003 | Schwalbe et al. |
| 6,544,229 B1 | 4/2003 | Danby et al. |
| 6,546,998 B2 | 4/2003 | Oh et al. |
| 6,554,789 B1 | 4/2003 | Brugger et al. |
| 6,572,576 B2 | 6/2003 | Brugger et al. |
| 6,572,641 B2 | 6/2003 | Brugger et al. |
| 6,575,927 B1 | 6/2003 | Weitzel et al. |
| 6,579,241 B2 | 6/2003 | Roeher |
| 6,579,253 B1 | 6/2003 | Burbank et al. |
| 6,581,906 B2 | 6/2003 | Pott et al. |
| 6,582,385 B2 | 6/2003 | Burbank et al. |
| 6,592,558 B2 | 7/2003 | Quah |
| 6,601,432 B1 | 8/2003 | Ericson et al. |
| 6,602,424 B1 | 8/2003 | Krämer et al. |
| 6,604,908 B1 | 8/2003 | Bryant et al. |
| 6,607,644 B1 | 8/2003 | Apffel, Jr. |
| 6,607,697 B1 | 8/2003 | Müller |
| 6,616,877 B2 | 9/2003 | Close et al. |
| 6,616,909 B1 | 9/2003 | Tonkovich et al. |
| 6,623,860 B2 | 9/2003 | Hu et al. |
| 6,630,068 B1 | 10/2003 | Vinci |
| 6,635,226 B1 | 10/2003 | Tso et al. |
| 6,640,611 B2 | 11/2003 | Ericson et al. |
| 6,649,046 B2 | 11/2003 | Chevallet |
| 6,649,063 B2 | 11/2003 | Brugger et al. |
| 6,652,627 B1 | 11/2003 | Tonkovich et al. |
| 6,653,841 B1 | 11/2003 | Koerdt et al. |
| 6,654,660 B1 | 11/2003 | Singh et al. |
| 6,666,840 B1 | 12/2003 | Falkvall et al. |
| 6,666,909 B1 | 12/2003 | Tegrotenhuis et al. |
| 6,672,502 B1 | 1/2004 | Paul et al. |
| 6,673,311 B1 | 1/2004 | Sotoyama et al. |
| 6,676,621 B1 | 1/2004 | Menninger |
| 6,676,835 B2 | 1/2004 | O'Connor et al. |
| 6,684,710 B2 | 2/2004 | Chevallet et al. |
| 6,685,831 B2 | 2/2004 | Dönig et al. |
| 6,686,946 B2 | 2/2004 | Masuda et al. |
| 6,688,381 B2 | 2/2004 | Pence et al. |
| 6,695,807 B2 | 2/2004 | Bell et al. |
| 6,716,356 B2 | 4/2004 | Collins et al. |
| 6,730,233 B2 | 5/2004 | Pedrazzi |
| 6,731,216 B2 | 5/2004 | Ho et al. |
| 6,733,676 B2 | 5/2004 | Takai |
| 6,736,789 B1 | 5/2004 | Spickermann |
| 6,738,052 B1 | 5/2004 | Manke et al. |
| 6,743,193 B2 | 6/2004 | Brugger et al. |
| 6,744,038 B2 | 6/2004 | Wang et al. |

(56) References Cited

U.S. PATENT DOCUMENTS

| | | |
|---|---|---|
| 6,746,514 B2 | 6/2004 | Bedingfield et al. |
| 6,749,814 B1 | 6/2004 | Bergh et al. |
| 6,767,333 B1 | 7/2004 | Müller et al. |
| 6,775,577 B2 | 8/2004 | Crnkovich et al. |
| 6,793,831 B1 | 9/2004 | Paul et al. |
| 6,797,056 B2 | 9/2004 | David |
| 6,804,991 B2 | 10/2004 | Balschat et al. |
| 6,806,947 B1 | 10/2004 | Ekdahl et al. |
| 6,811,707 B2 | 11/2004 | Rovatti et al. |
| 6,814,547 B2 | 11/2004 | Childers et al. |
| 6,814,726 B1 | 11/2004 | Lauer |
| 6,814,859 B2 | 11/2004 | Koehler et al. |
| 6,818,179 B1 | 11/2004 | Edgson et al. |
| 6,821,432 B2 | 11/2004 | Metzner |
| 6,827,698 B1 | 12/2004 | Kleinekofort |
| 6,830,693 B2 | 12/2004 | Govoni et al. |
| 6,838,156 B1 | 1/2005 | Neyer et al. |
| 6,852,231 B2 | 2/2005 | Ivansons et al. |
| 6,858,137 B2 | 2/2005 | Hahmann et al. |
| 6,863,867 B2 | 3/2005 | Vanden Bussche et al. |
| 6,868,309 B1 | 3/2005 | Begelman |
| 6,869,538 B2 | 3/2005 | Yu et al. |
| 6,871,838 B2 | 3/2005 | Raines et al. |
| 6,877,713 B1 | 4/2005 | Gray et al. |
| 6,878,283 B2 | 4/2005 | Thompson |
| 6,880,034 B2 | 4/2005 | Manke et al. |
| 6,881,344 B2 | 4/2005 | Vasta et al. |
| 6,889,556 B2 | 5/2005 | Steger |
| 6,892,781 B2 | 5/2005 | Mcherron et al. |
| 6,903,332 B2 | 6/2005 | Weiss et al. |
| 6,905,479 B1 | 6/2005 | Bouchard et al. |
| 6,911,262 B2 | 6/2005 | Sallavanti et al. |
| 6,913,877 B1 | 7/2005 | Chaplen et al. |
| 6,929,751 B2 | 8/2005 | Bowman, Jr. et al. |
| 6,936,031 B2 | 8/2005 | Caleffi |
| 6,939,111 B2 | 9/2005 | Huitt et al. |
| 6,939,471 B2 | 9/2005 | Gross et al. |
| 6,952,963 B2 | 10/2005 | Delnevo |
| 6,953,323 B2 | 10/2005 | Childers et al. |
| 6,955,655 B2 | 10/2005 | Burbank et al. |
| 6,967,002 B1 | 11/2005 | Edgson et al. |
| 6,974,301 B2 | 12/2005 | Suzuki et al. |
| 6,976,964 B2 | 12/2005 | Chevallet et al. |
| 6,979,309 B2 | 12/2005 | Burbank et al. |
| 6,981,522 B2 | 1/2006 | O'Connor et al. |
| 6,986,428 B2 | 1/2006 | Hester et al. |
| 6,989,134 B2 | 1/2006 | Tonkovich et al. |
| 6,994,829 B2 | 2/2006 | Whyatt et al. |
| 7,004,924 B1 | 2/2006 | Brugger et al. |
| 7,014,705 B2 | 3/2006 | David |
| 7,021,148 B2 | 4/2006 | Kuhn et al. |
| 7,022,098 B2 | 4/2006 | Wariar et al. |
| 7,029,456 B2 | 4/2006 | Ware et al. |
| 7,033,498 B2 | 4/2006 | Wong |
| 7,033,539 B2 | 4/2006 | Krensky et al. |
| 7,040,142 B2 | 5/2006 | Burbank |
| 7,044,432 B2 | 5/2006 | Beden et al. |
| 7,044,927 B2 | 5/2006 | Mueller et al. |
| 7,063,512 B2 | 6/2006 | Haesloop et al. |
| 7,070,589 B2 | 7/2006 | Lolachi et al. |
| 7,074,191 B2 | 7/2006 | Bosetto et al. |
| 7,087,033 B2 | 8/2006 | Brugger et al. |
| 7,087,036 B2 | 8/2006 | Busby et al. |
| 7,094,345 B2 | 8/2006 | Gilbert et al. |
| 7,112,273 B2 | 9/2006 | Weigel et al. |
| 7,114,701 B2 | 10/2006 | Peppel |
| 7,115,206 B2 | 10/2006 | Chevallet et al. |
| 7,115,228 B2 | 10/2006 | Lundtveit et al. |
| 7,118,920 B2 | 10/2006 | Brophy et al. |
| 7,121,815 B2 | 10/2006 | Knuth et al. |
| 7,122,149 B2 | 10/2006 | Li et al. |
| 7,122,156 B2 | 10/2006 | Bergh et al. |
| 7,125,540 B1 | 10/2006 | Wegeng et al. |
| 7,131,956 B1 | 11/2006 | Pirazzoli et al. |
| 7,147,615 B2 | 12/2006 | Wariar et al. |
| 7,150,815 B2 | 12/2006 | Ashmead et al. |
| 7,152,469 B2 | 12/2006 | Milleker et al. |
| 7,163,531 B2 | 1/2007 | Seese et al. |
| 7,166,084 B2 | 1/2007 | Utterberg |
| 7,168,334 B1 | 1/2007 | Drott |
| 7,170,591 B2 | 1/2007 | Ohishi et al. |
| 7,175,697 B2 | 2/2007 | Neri |
| 7,186,342 B2 | 3/2007 | Pirazzoli et al. |
| 7,188,151 B2 | 3/2007 | Kumar et al. |
| 7,211,442 B2 | 5/2007 | Gilbert et al. |
| 7,214,312 B2 | 5/2007 | Brugger et al. |
| 7,217,108 B2 | 5/2007 | Herwig et al. |
| 7,217,364 B2 | 5/2007 | Lauer et al. |
| 7,223,262 B2 | 5/2007 | Brehm et al. |
| 7,223,338 B2 | 5/2007 | Duchamp et al. |
| 7,232,418 B2 | 6/2007 | Neri et al. |
| 7,238,164 B2 | 7/2007 | Childers et al. |
| 7,247,146 B2 | 7/2007 | Tonelli et al. |
| 7,279,134 B2 | 10/2007 | Chan et al. |
| 7,291,123 B2 | 11/2007 | Baraldi et al. |
| 7,306,197 B2 | 12/2007 | Parrino et al. |
| 7,314,061 B2 | 1/2008 | Peppel |
| 7,316,780 B1 | 1/2008 | Fendya et al. |
| 7,337,674 B2 | 3/2008 | Burbank et al. |
| 7,341,568 B2 | 3/2008 | Zhang |
| 7,354,426 B2 | 4/2008 | Young |
| 7,355,685 B2 | 4/2008 | Scibona et al. |
| 7,378,280 B2 | 5/2008 | Quake et al. |
| 7,381,195 B2 | 6/2008 | Mori et al. |
| 7,393,337 B2 | 7/2008 | Tonelli et al. |
| 7,402,249 B2 | 7/2008 | Ikeda |
| 7,469,716 B2 | 12/2008 | Parrino et al. |
| 7,470,265 B2 | 12/2008 | Brugger et al. |
| 7,488,301 B2 | 2/2009 | Beden et al. |
| 7,488,447 B2 | 2/2009 | Sternby |
| 7,493,824 B2 | 2/2009 | Brucksch et al. |
| 7,494,590 B2 | 2/2009 | Felding et al. |
| 7,503,908 B2 | 3/2009 | Bartholomew |
| 7,507,380 B2 | 3/2009 | Chang et al. |
| 7,510,545 B2 | 3/2009 | Peppel |
| 7,517,332 B2 | 4/2009 | Tonelli et al. |
| 7,517,387 B2 | 4/2009 | Chevallet et al. |
| 7,520,919 B2 | 4/2009 | Caleffi |
| 7,537,687 B2 | 5/2009 | Toyoda et al. |
| 7,544,300 B2 | 6/2009 | Brugger et al. |
| 7,551,043 B2 | 6/2009 | Nguyen et al. |
| 7,559,911 B2 | 7/2009 | Giannella |
| 7,575,562 B2 | 8/2009 | Oishi et al. |
| 7,575,564 B2 | 8/2009 | Childers |
| 7,591,449 B2 | 9/2009 | Raines et al. |
| 7,603,907 B2 | 10/2009 | Reiter et al. |
| 7,615,035 B2 | 11/2009 | Peppel |
| 7,618,531 B2 | 11/2009 | Sugioka et al. |
| 7,622,043 B2 | 11/2009 | Sawada et al. |
| 7,632,470 B2 | 12/2009 | Tabata et al. |
| 7,647,834 B2 | 1/2010 | O'Mahony et al. |
| 7,648,474 B2 | 1/2010 | Paolini et al. |
| 7,648,476 B2 | 1/2010 | Bock et al. |
| 7,648,792 B2 | 1/2010 | Kaschmitter et al. |
| 7,656,527 B2 | 2/2010 | Scarpaci |
| 7,661,294 B2 | 2/2010 | Dam |
| 7,671,974 B2 | 3/2010 | O'Mahony et al. |
| 7,682,328 B2 | 3/2010 | Han et al. |
| 7,686,778 B2 | 3/2010 | Burbank et al. |
| 7,699,992 B2 | 4/2010 | Sternby |
| 7,708,714 B2 | 5/2010 | Connell et al. |
| 7,713,226 B2 | 5/2010 | Ash et al. |
| 7,726,361 B2 | 6/2010 | Bartholomew |
| 7,727,220 B2 | 6/2010 | Wieslander et al. |
| 7,744,553 B2 | 6/2010 | Kelly et al. |
| 7,749,184 B2 | 7/2010 | Cavalcanti et al. |
| 7,758,082 B2 | 7/2010 | Weigel et al. |
| 7,758,547 B2 | 7/2010 | Tonelli et al. |
| 7,771,379 B2 | 8/2010 | Treu |
| 7,771,380 B2 | 8/2010 | Jönsson et al. |
| 7,775,986 B2 | 8/2010 | Roeher et al. |
| 7,776,219 B2 | 8/2010 | Brugger et al. |
| 7,780,848 B2 | 8/2010 | Kim et al. |
| 7,788,038 B2 | 8/2010 | Oshita et al. |

(56) References Cited

U.S. PATENT DOCUMENTS

| | | |
|---|---|---|
| 7,790,029 B2 | 9/2010 | Dannenmaier et al. |
| 7,794,141 B2 | 9/2010 | Perry et al. |
| 7,794,419 B2 | 9/2010 | Paolini et al. |
| 7,801,746 B2 | 9/2010 | Moll et al. |
| 7,815,852 B2 | 10/2010 | Sternby |
| 7,824,354 B2 | 11/2010 | Vinci et al. |
| 7,873,489 B2 | 1/2011 | Dolgos et al. |
| 7,896,831 B2 | 3/2011 | Sternby et al. |
| 7,901,579 B2 | 3/2011 | Brugger et al. |
| 7,913,751 B2 | 3/2011 | Zwittig |
| 7,918,993 B2 | 4/2011 | Harraway |
| 7,922,899 B2 | 4/2011 | Vasta et al. |
| 7,955,504 B1 | 6/2011 | Jovanovic et al. |
| 7,968,250 B2 | 6/2011 | Kaschmitter et al. |
| 8,002,727 B2 | 8/2011 | Brugger et al. |
| 8,012,114 B2 | 9/2011 | Daniel et al. |
| 8,075,509 B2 | 12/2011 | Molducci et al. |
| 8,105,265 B2 | 1/2012 | Demers et al. |
| 8,128,822 B2 | 3/2012 | Browning et al. |
| 8,137,554 B2 | 3/2012 | Jovanovic et al. |
| 8,182,440 B2 | 5/2012 | Cruz et al. |
| 8,182,691 B2 | 5/2012 | Stahl |
| 8,190,651 B2 | 5/2012 | Treu et al. |
| 8,192,387 B2 | 6/2012 | Brugger et al. |
| 8,210,049 B2 | 7/2012 | Brugger |
| 8,235,931 B2 | 8/2012 | Burbank et al. |
| 8,236,599 B2 | 8/2012 | Chang et al. |
| 8,267,881 B2 | 9/2012 | O'Mahony et al. |
| 8,273,245 B2 | 9/2012 | Jovanovic et al. |
| 8,293,113 B2 | 10/2012 | Jönsson et al. |
| 8,293,114 B2 | 10/2012 | Jönsson et al. |
| 8,298,427 B2 | 10/2012 | Ficheux et al. |
| 8,323,492 B2 | 12/2012 | Childers et al. |
| 8,329,030 B2 | 12/2012 | Childers et al. |
| 8,343,085 B2 | 1/2013 | Toyoda et al. |
| 8,394,046 B2 | 3/2013 | Nuernberger et al. |
| 8,414,182 B2 | 4/2013 | Paul et al. |
| 8,419,945 B2 | 4/2013 | Browning et al. |
| 8,449,487 B2 | 5/2013 | Hovland et al. |
| 8,460,228 B2 | 6/2013 | Burbank et al. |
| 8,475,398 B2 | 7/2013 | O'Mahony |
| 8,491,518 B2 | 7/2013 | Schnell et al. |
| 8,496,824 B2 | 7/2013 | Remkes et al. |
| 8,501,009 B2 | 8/2013 | Peterson et al. |
| 8,506,536 B2 | 8/2013 | Schnell |
| 8,512,553 B2 | 8/2013 | Cicchello et al. |
| 8,512,554 B2 | 8/2013 | Yu et al. |
| 8,524,086 B2 | 9/2013 | Peterson et al. |
| 8,529,491 B2 | 9/2013 | Beiriger |
| 8,603,020 B2 | 12/2013 | Roger et al. |
| 8,608,658 B2 | 12/2013 | Burbank et al. |
| 8,647,290 B2 | 2/2014 | Masala et al. |
| 8,679,348 B2 | 3/2014 | Burbank et al. |
| 8,685,251 B2 | 4/2014 | Smejtek et al. |
| 8,753,515 B2 | 6/2014 | Curtis et al. |
| 8,801,922 B2 | 8/2014 | Wrazel et al. |
| 8,840,581 B2 | 9/2014 | McGill et al. |
| 9,024,746 B2 | 5/2015 | Burbank et al. |
| 9,097,370 B2 | 8/2015 | Schnell et al. |
| 9,138,687 B2 | 9/2015 | Peterson et al. |
| 9,328,969 B2 | 5/2016 | Wrazel et al. |
| 9,402,945 B2 | 8/2016 | Hogard et al. |
| 2002/0023879 A1 | 2/2002 | Hadden |
| 2002/0032398 A1 | 3/2002 | Steele et al. |
| 2002/0108859 A1 | 8/2002 | Wang et al. |
| 2002/0108869 A1 | 8/2002 | Savtchenko |
| 2002/0115200 A1 | 8/2002 | Zou et al. |
| 2002/0162784 A1 | 11/2002 | Kohlheb et al. |
| 2002/0187069 A1 | 12/2002 | Levin et al. |
| 2003/0010717 A1 | 1/2003 | Brugger et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0138349 A1 | 7/2003 | Robinson et al. |
| 2003/0156991 A1 | 8/2003 | Halas et al. |
| 2003/0163077 A1 | 8/2003 | Kim et al. |
| 2003/0183345 A1 | 10/2003 | Soberay |
| 2003/0220598 A1 | 11/2003 | Busby et al. |
| 2004/0004589 A1 | 1/2004 | Shih |
| 2004/0008370 A1 | 1/2004 | Keane et al. |
| 2004/0012122 A1 | 1/2004 | Nagaoka et al. |
| 2004/0016700 A1 | 1/2004 | Kellam et al. |
| 2004/0020286 A1 | 2/2004 | Blakley et al. |
| 2004/0022691 A1 | 2/2004 | Allen et al. |
| 2004/0035452 A1 | 2/2004 | Ma |
| 2004/0035462 A1 | 2/2004 | McCarty et al. |
| 2004/0072278 A1 | 4/2004 | Chou et al. |
| 2004/0084370 A1 | 5/2004 | Singh et al. |
| 2004/0084371 A1 | 5/2004 | Kellam et al. |
| 2004/0086427 A1 | 5/2004 | Childers et al. |
| 2004/0125689 A1 | 7/2004 | Ehrfeld et al. |
| 2004/0157096 A1 | 8/2004 | Peterson |
| 2004/0158189 A1 | 8/2004 | Tonelli et al. |
| 2004/0208751 A1 | 10/2004 | Lazar et al. |
| 2004/0215129 A1 | 10/2004 | Edgson et al. |
| 2004/0256230 A1 | 12/2004 | Yager et al. |
| 2005/0006296 A1 | 1/2005 | Sullivan et al. |
| 2005/0007748 A1 | 1/2005 | Callahan et al. |
| 2005/0070837 A1 | 3/2005 | Ferrarini et al. |
| 2005/0074834 A1 | 4/2005 | Chaplen et al. |
| 2005/0082225 A1 | 4/2005 | Kreymann |
| 2005/0126211 A1 | 6/2005 | Drost et al. |
| 2005/0129580 A1 | 6/2005 | Swinehart et al. |
| 2005/0131332 A1 | 6/2005 | Kelly et al. |
| 2005/0145497 A1 | 7/2005 | Gilbert et al. |
| 2005/0179748 A1 | 8/2005 | Malik et al. |
| 2005/0202557 A1 | 9/2005 | Borenstein et al. |
| 2006/0079698 A1 | 4/2006 | Joshi et al. |
| 2006/0157413 A1 | 7/2006 | Bene et al. |
| 2006/0200064 A1 | 9/2006 | Gross et al. |
| 2006/0266692 A1 | 11/2006 | Foster et al. |
| 2007/0020400 A1 | 1/2007 | Chang |
| 2007/0029365 A1 | 2/2007 | Paul et al. |
| 2007/0119771 A1 | 5/2007 | Schukar et al. |
| 2007/0125489 A1 | 6/2007 | Paul et al. |
| 2007/0128707 A1 | 6/2007 | Rorrer et al. |
| 2007/0131403 A1 | 6/2007 | Vetrovec et al. |
| 2007/0158249 A1 | 7/2007 | Ash |
| 2007/0158268 A1 | 7/2007 | Decomo |
| 2007/0184576 A1 | 8/2007 | Chang et al. |
| 2007/0215644 A1 | 9/2007 | Otis et al. |
| 2007/0278155 A1 | 12/2007 | Lo et al. |
| 2007/0295651 A1 | 12/2007 | Martinez et al. |
| 2008/0006040 A1 | 1/2008 | Peterson et al. |
| 2008/0009780 A1 | 1/2008 | Leonard et al. |
| 2008/0097274 A1 | 4/2008 | Neri et al. |
| 2008/0108122 A1 | 5/2008 | Paul et al. |
| 2008/0108930 A1 | 5/2008 | Weitzel et al. |
| 2008/0149563 A1 | 6/2008 | Ash |
| 2008/0196725 A1 | 8/2008 | Mele |
| 2008/0200858 A1 | 8/2008 | Ichiishi et al. |
| 2008/0296226 A1 | 12/2008 | Gotch |
| 2009/0008331 A1 | 1/2009 | Wilt et al. |
| 2009/0012452 A1 | 1/2009 | Slepicka et al. |
| 2009/0038393 A1 | 2/2009 | Chaung et al. |
| 2009/0087326 A1 | 4/2009 | Voltenburg et al. |
| 2009/0092526 A1 | 4/2009 | Miller |
| 2009/0095679 A1 | 4/2009 | Demers et al. |
| 2009/0101549 A1 | 4/2009 | Kamen et al. |
| 2009/0101576 A1 | 4/2009 | Rohde et al. |
| 2009/0114595 A1 | 5/2009 | Wallenas et al. |
| 2009/0124963 A1 | 5/2009 | Hogard et al. |
| 2009/0165366 A1 | 7/2009 | Jovanovic et al. |
| 2009/0211977 A1 | 8/2009 | Miller |
| 2009/0306573 A1 | 12/2009 | Gagner et al. |
| 2009/0309835 A1 | 12/2009 | Levin et al. |
| 2010/0018923 A1 | 1/2010 | Rohde et al. |
| 2010/0022934 A1 | 1/2010 | Hogard |
| 2010/0051552 A1 | 3/2010 | Rohde et al. |
| 2010/0078385 A1 | 4/2010 | Kawarabata et al. |
| 2010/0192686 A1 | 8/2010 | Kamen et al. |
| 2010/0271296 A1 | 10/2010 | Kopychev et al. |
| 2010/0292627 A1 | 11/2010 | Caleffi et al. |
| 2010/0292657 A1 | 11/2010 | Fontanazzi et al. |

(56) References Cited

U.S. PATENT DOCUMENTS

| | | |
|---|---|---|
| 2010/0321046 A1 | 12/2010 | Randall et al. |
| 2010/0326914 A1 | 12/2010 | Drost et al. |
| 2011/0005986 A1 | 1/2011 | Kelly et al. |
| 2011/0105979 A1 | 5/2011 | Schlaeper et al. |
| 2011/0106466 A1 | 5/2011 | Furmanski et al. |
| 2011/0132841 A1 | 6/2011 | Rohde et al. |
| 2011/0186517 A1 | 8/2011 | Hedmann et al. |
| 2011/0189048 A1 | 8/2011 | Curtis et al. |
| 2011/0257579 A1 | 10/2011 | Rossi et al. |
| 2011/0295175 A1 | 12/2011 | Felder et al. |
| 2012/0029937 A1 | 2/2012 | Neftel et al. |
| 2012/0065581 A1 | 3/2012 | Childers et al. |
| 2012/0103902 A1 | 5/2012 | Childers et al. |
| 2012/0138533 A1 | 6/2012 | Curtis et al. |
| 2012/0292246 A1 | 11/2012 | Jovanovic et al. |
| 2012/0318740 A1 | 12/2012 | Ekdahl et al. |
| 2013/0018301 A1 | 1/2013 | Weaver et al. |
| 2013/0020237 A1 | 1/2013 | Wilt et al. |
| 2013/0056419 A1 | 3/2013 | Curtis |
| 2013/0186829 A1 | 7/2013 | Callan et al. |
| 2014/0021111 A1 | 1/2014 | Roger et al. |
| 2014/0069861 A1 | 3/2014 | Browning et al. |
| 2014/0209540 A1 | 7/2014 | Smejtek et al. |
| 2014/0291243 A1 | 10/2014 | Curtis et al. |
| 2014/0299545 A1 | 10/2014 | Wrazel et al. |
| 2015/0314055 A1 | 11/2015 | Hogard et al. |
| 2015/0328386 A1 | 11/2015 | Peterson et al. |
| 2015/0343128 A1 | 12/2015 | Hogard et al. |
| 2015/0343131 A1 | 12/2015 | Hogard et al. |
| 2015/0343132 A1 | 12/2015 | Hogard et al. |
| 2015/0343133 A1 | 12/2015 | Hogard et al. |
| 2015/0354906 A1 | 12/2015 | Miller |
| 2016/0082172 A1 | 3/2016 | Miller et al. |

FOREIGN PATENT DOCUMENTS

| | | |
|---|---|---|
| DE | 69217519 T2 | 6/1997 |
| EP | 0165751 A2 | 12/1985 |
| EP | 0324922 A2 | 7/1989 |
| EP | 0679100 A1 | 11/1995 |
| EP | 0796997 A1 | 9/1997 |
| EP | 0547025 B2 | 6/2002 |
| GB | 1289738 A | 9/1972 |
| JP | 59-58002 | 4/1984 |
| JP | 60-143803 | 7/1985 |
| JP | 2002143298 | 5/2002 |
| JP | 2007268490 A | 10/2007 |
| JP | 2007529707 A | 10/2007 |
| WO | WO00/16916 A1 | 3/2000 |
| WO | WO00/25843 A1 | 5/2000 |
| WO | WO02/40874 A1 | 5/2002 |
| WO | WO02/076529 A1 | 10/2002 |
| WO | WO03/076661 A1 | 9/2003 |
| WO | WO2006/039293 A2 | 4/2006 |
| WO | WO2007/089855 A2 | 8/2007 |
| WO | WO2008/027967 A1 | 3/2008 |
| WO | WO2008/106191 A2 | 9/2008 |
| WO | WO2010/027435 A1 | 3/2010 |
| WO | WO2010/062698 A2 | 6/2010 |
| WO | WO2010/085764 | 7/2010 |

OTHER PUBLICATIONS

Anglés et al., "Plasticized starch/Tunicin Whiskers Nanocomposite Materials. 2. Mechanical behavior," Macromolecules, 34, pp. 2921-2931, Mar. 2001.

California Energy Commission; Development of Supported Polymeric Liquid Membrane Technology for Aqueous MTBE Mitigation, EPRI, Palo Alto, CA, California Energy Commission, Sacramento, CA: Doc. No. 1006577; 70 pgs.; Jul. 2002.

Demura et al., "Ductile Thin Foil of Ni3Al," Mechanical Properties of Structural Films, ASTM International Nov. 2000 Symposium (Orlando, FL), pp. 248-261, published Oct. 1, 2001.

Favier et al.; Nanocomposite materials from latex and cellulose whiskers; Polymers for Advanced Technologies; 6; pp. 351-355; Jan. 1995.

Federal Energy Technology Center, "Technology Development Through Industrial Partnerships," (Tech. Dev. Data Sheet), 12 pgs., Sep. 1998.

Grunert et al., "Progress in the Development of Cellulose Reinforced Nanocomposites," PMSE Preprints 2000, 82, 232, 2 pgs., Mar. 2000.

Haas, "Further development of MMW and SMMW platelet feed horn arrays," Astron. Soc. Pac. Conf. Ser., vol. 75, pp. 99-105, Multi-Feed Systems for Radio Telescopes, Workshop held in Tucson, Arizona, May 16-18, 1994.

Introtek International; Drip chamber liquid level sensor (sales literature); 2 pages; retrieved from the internet (http://www.introtek.com/PDFs/l/DDS-14.0_DripDetectSensor.pdf); © Jan. 1, 2009.

Koeneman et al., "Feasibility of Micro Power Supplies for MEMS," (pre-publication copy) J. MicroElectoMechanical Sys., 6(4), pp. 355-362, Dec. 1997.

Morin et al., "Nanocomposites of Chitin Whiskers from Riftia Tubes and Poly (caprolactone)," Macromolecules, vol. 35, pp. 2190-2199, Feb. 2002.

Nakamura et al., "Research on Pressure Welding Conditions of Various Work Metals (Effects of Contact Pressure, Surface Expansion Ratio and Temperature)," JSME International Journal, Series III 31(3), 612-617, Sep. 1988.

Nakao et al., "Diffusion Bonding of Intermetallic Compound TiAl," ISIJ International, 31(10), 1260-1266, Oct. 1991.

Oddy et al., "Electrokinetic Instability Micromixing," Anal. Chem., 73(24), pp. 5822-5832, Dec. 2001.

Omega Engineering Inc.; Load Cell (definition, information); 3 pgs; retrieved from the internet on Jun. 17, 2015 (http://www.omega.com/prodinfo/LoadCells.html).

Orts et al., "Effect of Fiber Source on Cellulose Reinforced Polymer Nanocomposites," ANTEC 2004: Conference Proceedings, 62nd Annual Tech. Conference; Chicago, IL, pp. 2427-2431, May 2004.

Paillet et al., "Chitin Whisker Reinforced Thermoplastic Nanocomposites," Macromolecules, vol. 34, No. 19, pp. 6527-6530, Sep. 2001.

Paul et al., "Microlamination for Microtechnology-based Energy, Chemical, and Biological Systems," ASME IMECE, ASE vol. 39, pp. 45-52, Nashville, Tennessee, Nov. 15-20, 1999.

Pluess, "Application of Controlled Thermal Expansion in Diffusion Bonding for the High-Volume Microlamination of MECS Devices," Thesis (MS), Oregon State University, 193 pgs., Sep. 2004.

Porter et al.; Cost drivers in microlamination based on a high volume production system design; ASME 2002 Conf. Proc.; New Orleans, Louisiana; pp. 267-274; Nov. 17-22, 2002.

Sharma et al., "The Application of Surface Mount Technology to Multi-Scale Process Intensification," ASPE, pp. 1-4, Oct. 2003.

Stroock et al., "Chaotic Mixer for Microchannels," Science, 295, pp. 647-651, Jan. 2002.

Thorsen et al.; Microfluidic Large-Scale Integration; Science; 298; pp. 580-584; Oct. 18, 2002.

Wegeng et al., "Chemical system miniaturization," Proceedings of the AIChE Spring National Meeting, pp. 1-13, Feb. 1996.

DIALYSIS SYSTEM WITH ULTRAFILTRATION CONTROL

CROSS REFERENCE TO RELATED APPLICATIONS

This application is a continuation of U.S. application Ser. No. 14/305,952, filed Jun. 16, 2014, which is a continuation of U.S. application Ser. No. 12/795,498, filed Jun. 7, 2010, now U.S. Pat. No. 8,753,515, that in turn claims priority to U.S. Provisional Application No. 61/267,043, filed Dec. 5, 2009. Priority of the filing date of Dec. 5, 2009, is hereby claimed, and the disclosures of the aforementioned patent applications are hereby incorporated by reference, each in its entirety.

BACKGROUND

Chronic dialysis has been performed on patients with kidney failure since the early 1960's. A dialyzer is a device for cleansing blood through hemodialysis by a process of diffusion and/or convection of waste products, dissolved solutes and fluid from the blood across a semi permeable membrane into a dialysis solution known as dialysate. A dialysis system is an assembly that includes the dialyzer and associated equipment to support the dialyzer, such a plumbing and pumps.

Diffusion is the principal mechanism in which dialysis removes waste products such as urea, creatinine, phosphate and uric acid, among others, from the blood. A differential between the chemical composition of the dialysate and the chemical composition of the blood causes the waste products to be drawn through the semi-permeable membrane from the blood into the dialysate. Ultrafiltration is a process in dialysis where fluid is caused to move across the membrane from the blood into the dialysate for the purpose of removing excess fluid from the patient's blood stream. Along with water, some solutes are also drawn across via convection rather than diffusion. Ultrafiltration is a result of a pressure differential between the blood compartment of the dialyzer and the dialysate compartment of the dialyzer where fluid will move from a higher pressure to a lower pressure. In some circumstances, by design or unintentionally, fluid in the dialysate compartment is higher than the blood compartment, causing fluid to move from the dialysate compartment into the blood compartment. This is commonly referred to as reverse ultrafiltration.

It would be convenient for a patient to be able to perform dialysis in his or her home. Unfortunately, current dialysis systems are large in size, making them generally unsuitable for use in a patient's home. Current dialysis systems are also energy-inefficient in that they use large amounts of energy and require enormous amounts of water for proper use. Although some home dialysis systems are available, they generally use complex flow-balancing technology that is relatively expensive to manufacture and most systems are designed with a system of solenoid valves that create high noise levels. As a result, most dialysis treatments are performed at dialysis centers.

SUMMARY

In view of the foregoing, there is a need for improved dialysis systems that are smaller, more portable, consume less water and that provide precise control over a level of ultrafiltration. Disclosed are systems and methods for performing hemodialysis that include fluid handling systems and provide accurate control over the type and level of hemodialysis being performed. The system includes a first pump for pumping dialysate into a dialyzer and a second pump for pumping dialysate out of the dialyzer. The system also includes a third pump that provides improved control of a level of ultrafiltration, hemodiafiltration, or both, as described in detail below.

In one aspect, there is disclosed a method of performing dialysis, comprising: operating a first pump to pump dialysate at a first flow rate through a fluid inlet pathway into a dialyzer; operating a second pump to pump the dialysate through a fluid outlet pathway out of the dialyzer; operating a third pump to pump the dialysate through the fluid outlet pathway in cooperation with the second pump, wherein the second and third pumps cooperate to collectively achieve a second flow rate through the fluid outlet pathway from the dialyzer; and pumping blood through the dialyzer in communication with the dialysate such that the dialyzer dialyzes the blood.

In another aspect, there is disclosed a method of performing dialysis, comprising: providing a dialysis system having an inlet conduit through which fluid flows in an inward direction toward a dialyzer and an outlet conduit through which fluid flows in an outward direction from the dialyzer; pumping fluid through the inlet conduit using a first pump; pumping fluid through the outlet conduit using a second pump; and using a third pump to supplement the pumping of the second pump through the outlet conduit.

In another aspect, there is disclosed a dialysis system, comprising: a dialyzer having a blood flow pathway through which blood flows; a fluid inlet pathway configured to provide incoming fluid to the dialyzer; a fluid outlet pathway configured to receive outgoing fluid from the dialyzer; a first pump coupled to the fluid inlet pathway and configured to pump the fluid through the fluid inlet pathway toward the dialyzer; a second pump coupled to the fluid outlet pathway and configured to pump the fluid through the fluid outlet pathway away from the dialyzer; and a third pump coupled to the fluid outlet pathway, the third pump configured to work in cooperation with the second pump to achieve a desired flow rate of fluid to or from the blood flowing through the dialyzer.

Other features and advantages should be apparent from the following description of various embodiments, which illustrate, by way of example, the principles of the disclosed devices and methods.

DETAILED DESCRIPTION

In order to promote an understanding of the principals of the disclosure, reference is made to the drawings and the embodiments illustrated therein. Nevertheless, it will be understood that the drawings are illustrative and no limitation of the scope of the disclosure is thereby intended. Any such alterations and further modifications in the illustrated embodiments, and any such further applications of the principles of the disclosure as illustrated herein are contemplated as would normally occur to one of ordinary skill in the art.

Figure 1A:
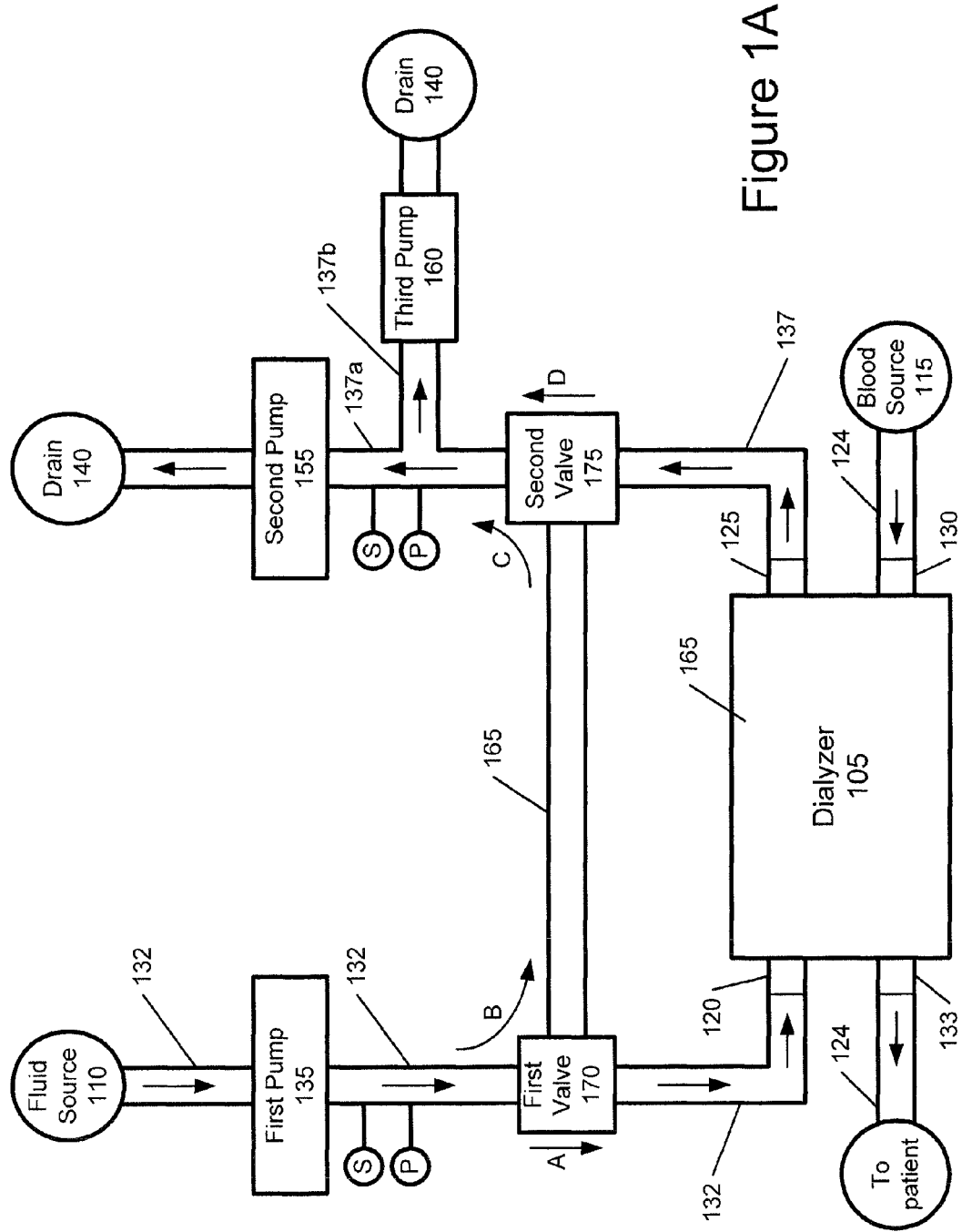
FIG. 1A shows a schematic view of a dialysis system adapted to perform dialysis of a patient's blood.

FIG. 1A shows a schematic view of a dialysis system adapted to perform hemodialysis of a patient's blood. The system includes an arrangement of three or more pumps that provide improved control over the type of hemodialysis being performed. By varying the relative pump speeds of the three pumps, an operator can vary the level of blood filtration and can also selectively achieve ultrafiltration and hemodiafiltration of the blood.

Ultrafiltration is a process in dialysis where fluid is caused to move across a dialyzer membrane via diffusion from the blood into the dialysate for the purpose of removing excess fluid from the patient's blood stream. Along with water, some solutes are also drawn across the membrane via convection rather than diffusion. Ultrafiltration is a result of a pressure differential between the blood compartment and the dialysate compartment where fluid will move from a higher pressure to a lower pressure.

In some circumstances, by design or unintentional, fluid in the dialysate compartment is higher than the blood compartment causing fluid to move from the dialysate compartment into the blood compartment. This is commonly referred to as reverse ultrafiltration. In hemodiafiltration a high level of ultrafiltration is created, greater than the amount required to remove fluid from the patient's blood, for the purpose of increasing convective solute transport across the membrane. The amount of fluid in excess of what is required to be removed from the patient's blood must therefore be returned to the blood stream in order to avoid an adverse blood reaction. This is accomplished by intentionally increasing the pressure in the dialysate compartment of the dialyzer to cause the appropriate amount of reverse ultrafiltration. This process of ultrafiltration alternating with reverse ultrafiltration is often referred to as "push-pull hemodiafiltration". This is a significant improvement over more common methods of hemodiafiltration where sterile fluid is administered to the patient in a location outside of the dialyzer.

The dialysis system includes a dialyzer 105 that is fluidly connected to a source 110 of fluid (such as dialysate) and also to a source 115 of blood to be dialyzed. The source 115 of blood may be a patient. The source 110 of fluid may be a dialysate preparation system that prepares dialysate for use in the dialysis system. The dialysate preparation system may include a water purification system that purifies water pursuant to systems and methods described in U.S. patent application Ser. No. 12/795,382, entitled "Fluid Purification System", filed Jun. 7, 2010, now U.S. Pat. No. 8,501,009, and which is incorporated by reference in its entirety. In addition, the dialyzer 105 may be at least partially configured with microfluidic pathways as described in U.S. patent application Ser. No. 12/795,371 entitled "Microfluidic Devices", filed Jun. 7, 2010, which claims priority to U.S. Provisional Application No. 61/220,117, filed Jun. 24, 2009, which applications are incorporated by reference in their entirety. U.S. patent application Ser. No. 12/795,444 entitled "Dialysis System", filed Jun. 7, 2010, now U.S. Pat. No. 8,801,922, is also incorporated by reference in its entirety. Dialysate flows into the dialyzer 105 through a fluid inlet 120 and out of the dialyzer 105 through a fluid outlet 125.

Blood flows through the dialyzer 105 via a blood flow pathway 124 that includes a blood inlet 130 into the dialyzer 105 and a blood outlet 133 out of the dialyzer. From the dialyzer 105, the blood flows back to the patient. The dialyzer 105 is described in more detail below.

The dialysis system includes plumbing that forms a plurality of fluid flow pathways, which may be any type of conduit through which a fluid such as dialysate may flow. The fluid flow pathways include an inlet pathway 132 through which a fluid such as unused dialysate flows from the source 110 toward and into the dialyzer 105. At least a first pump 135 is positioned along or in communication with the inlet pathway 132 for pumping the fluid toward the dialyzer 105 at a desired flow rate. One or more sensors S may be coupled to the fluid flow pathway for sensing one or more characteristics of the incoming fluid, such as pressure, flow rate, temperature, conductivity, etc. In addition, one or more sample ports P may be coupled to the fluid flow pathways that provide access to fluid flowing through the piping. FIG. 1 shows the sensors S and sample ports P coupled to the fluid flow pathways at specific locations, although the quantity and locations of the sensors S and sample ports P may vary.

The fluid flow pathways further include an outlet pathway 137 through which used dialysate flows out of the dialyzer 105 toward one or more drains 140. In some embodiments, the dialysate exiting the dialyzer may be used to pre-heat other incoming fluids in the system, such as the water stream entering the heat exchange and purification system, before reaching the drain 140. The outlet pathway 137 bifurcates into two or more outlet pathways including a main outlet pathway 137a and a secondary outlet pathway 1137b. At least a second pump 155 is positioned along or in communication with the main outlet pathway 137a for pumping the dialysate out of and away from the dialyzer 105 through the main outlet pathway 137a.

A third pump 160 is positioned along or in communication with the secondary outlet pathway 137b. The third pump 160 can be used to augment fluid flow through the fluid flow pathways such as to selectively achieve differentials in flow rates between the inflow pathway 132 and the outflow pathway 132 pursuant to achieving various types of dialysis, including hemodialysis, ultrafiltration, and hemodiafiltration, as described more fully below. The third pump pumps dialysate through the fluid flow pathways when the system is in dialysis mode. The third pump may also pump another fluid, such as water or disinfectant, when the system is in a different mode, such as in a calibration mode or in a cleaning mode. The third pump 160 can also be used to calibrate flow rates between the first pump 135 and the second pump 155, as described more fully below.

Figure 1B:
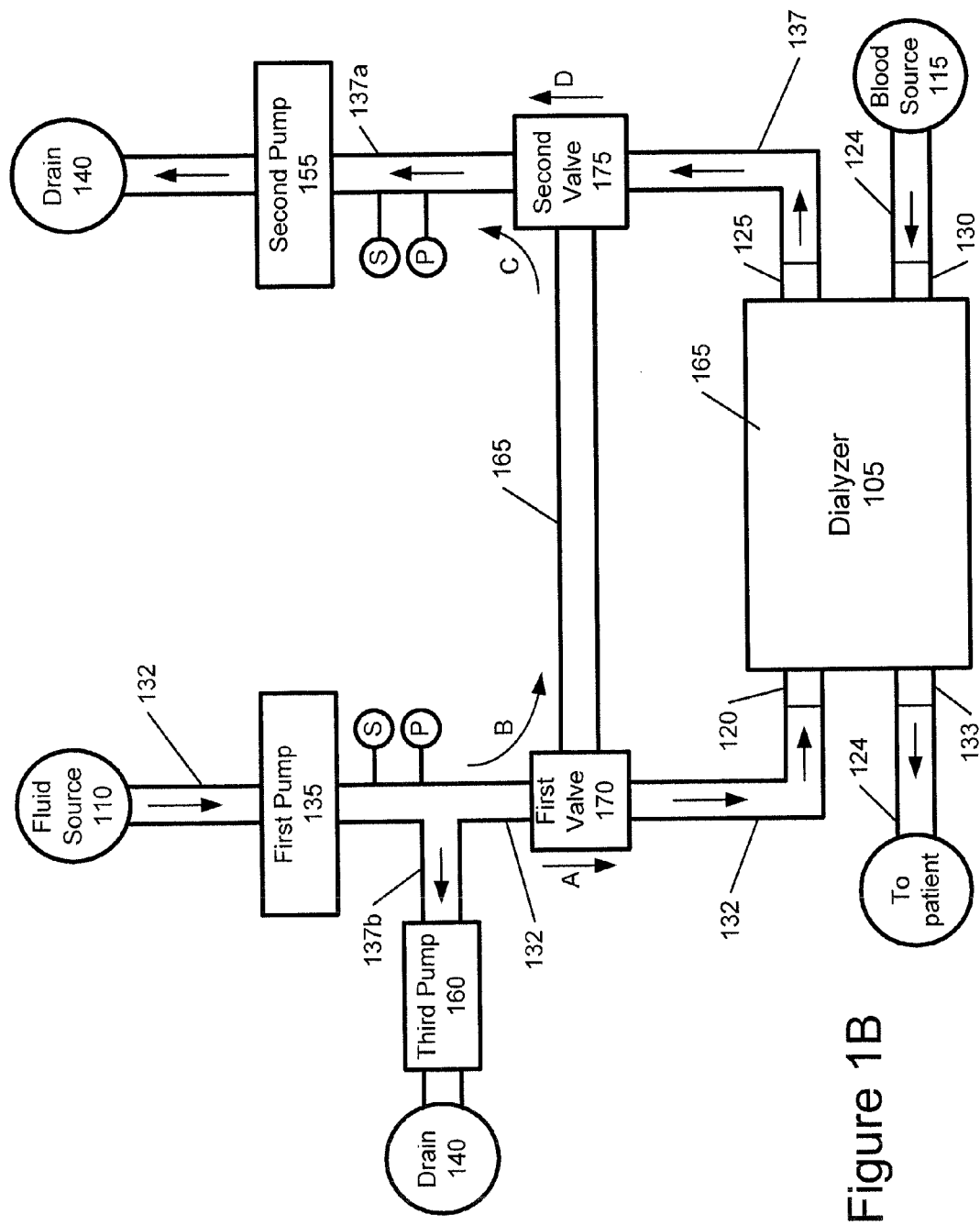
FIG. 1B shows a schematic view of another embodiment of a dialysis system.

In another embodiment, shown in FIG. 1B, the third pump 160 is positioned along the inflow pathway 132 upstream of the inlet 120 of the dialyzer 105. In this embodiment, the secondary outlet pathway 137 branches off the inlet pathway 132 at a location downstream of the first pump 135 and upstream of the first valve 170. The third pump 160 pumps fluid toward the drain 140. The embodiment of FIG. 1A may be more efficient than the embodiment of FIG. 1B because the third pump 160 in FIG. 1B pumps fresh, unused dialysate into the drain 140 while the third pump in FIG. 1A pumps used dialysate into the drain 140. In another embodiment, the third pump 160 and the second pump 155 are both positioned along a single, non-bifurcating outflow pathway.

Various types of pumps may be used for the first, second and third pumps. In an embodiment, the pumps are nutating pumps. On other embodiments, the pumps could be rotary lobe pumps, progressing cavity pumps, rotary gear pumps, piston pumps, diaphragm pumps, screw pumps, gear pumps, hydraulic pumps, vane pumps, regenerative (peripheral) pumps, or peristaltic pumps, or any combination thereof. Other types of pumps can also be used. The first pump 135 and the second pump 155 may be driven by a common shaft to ensure synchrony of the pump strokes and the volume of fluid pumped. It is understood that first pump 135 and the second pump 155 may also be fully independent from each other.

As mentioned, any of a variety of fluid conduits may be used to form the fluid flow pathways. In an embodiment, at least a portion of the fluid flow pathway is formed of piping having an inside diameter from ⅛ inch to ½ inch. The flow rate in the piping could range between about 50 ml/min to about 1,000 ml/min. In an embodiment, the flow rate is in the range of between about 100 ml/min and about 300 ml/min.

With reference again to FIG. 1A, the fluid flow pathways further include a bypass pathway 165 that fluidly directly connects the inlet pathway 132 and the outlet pathway 137. An exemplary purpose of the bypass pathway 165 is to provide a fluid flow pathway where fluid can flow into and out of the dialysis system and bypass the dialyzer 105, such as for flushing, cleaning or calibrating the system. In an embodiment, the junction between the inlet pathway 132 and bypass pathway 165 is located upstream of the fluid inlet 120 of the dialyzer 105, and the junction between the bypass pathway 165 and the outlet pathway is located downstream of the fluid outlet 125 of the dialyzer 105. However, other configurations of the bypass pathway 165 can be used to achieve bypassing of the dialyzer 105.

A first valve 170 is positioned at the junction between the inlet pathway 132 and the bypass pathway 165. A second valve 175 is positioned at the junction between the bypass pathway 165 and the outlet pathway 137. The first valve 170 and second valve 175 are three-way valves, such as solenoid valves, that can be used to selectively regulate fluid flow through the fluid flow pathways. That is, the first valve 170 can be set to either of two or more settings including (1) a dialysis setting wherein the first valve directs all incoming fluid along the inlet pathway 132 toward the dialyzer 105 (as represented by arrow A in FIG. 1) and prevents incoming fluid from flowing into the bypass pathway 165; or (2) a bypass setting wherein the first valve 170 diverts all the incoming fluid into the bypass pathway 165 (as represented by arrow B in FIG. 1) and the prevents incoming fluid from flowing past the first valve toward the dialyzer 105.

The second valve 175 can also be set to either of two settings including (1) a bypass setting wherein the second valve 175 directs incoming fluid from the bypass pathway 165 into the outlet pathway 137 (as represented by arrow C in FIG. 1); or (2) a dialysis setting wherein the second valve 175 closes flow from the bypass valve 165 such that outgoing fluid from the dialyzer outlet 125 continues to flow outward along the outlet pathway 137 (as represented by arrow D in FIG. 1.) The first valve 175 and the second valve 160 are generally both set in tandem to either the bypass setting or the dialysis setting. The system may include a control and safety system that ensures that the first and second valves are not set to incompatible settings.

The arrangement of the various components of the dialysis system shown in FIGS. 1A and 1B are exemplary and other arrangements are possible. For example, the flow pathways and the pumps may be placed in different locations along the flow pathways from what is shown in FIG. 1. In an embodiment, the third pump 160 is positioned in the flow pathway at a location upstream of the dialyzer 105 and downstream of the first valve 170 or the third pump can be positioned downstream of the dialyzer 105 and upstream of the second valve 175. Moreover, the system can employ more than three pumps.

Dialyzer and Various Forms of Dialysis

Figure 2:
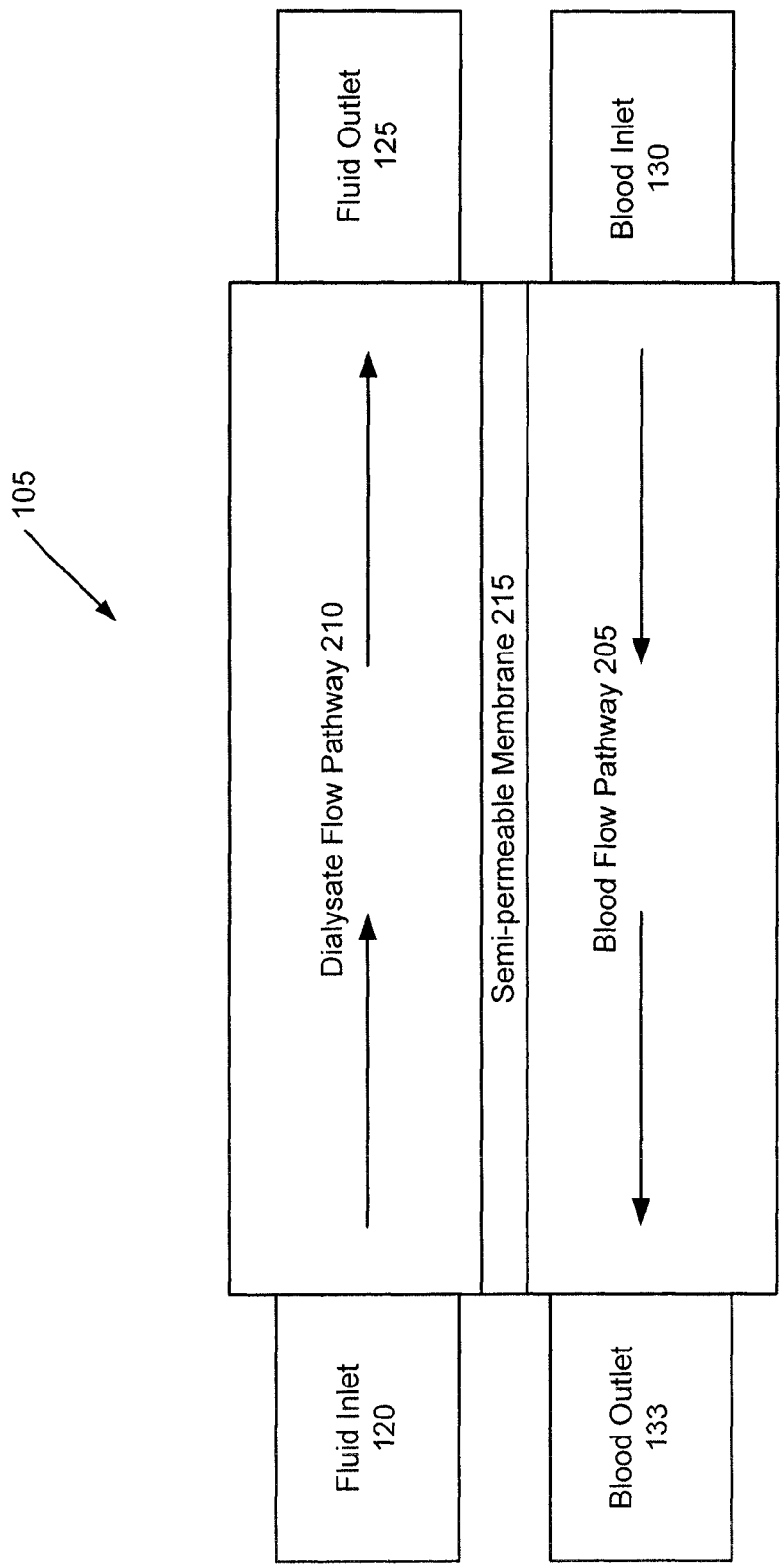
FIG. 2 is a schematic view of a dialyzer of the dialysis system.

FIG. 2 is a schematic, cross-sectional view of the dialyzer 105, which defines a blood compartment having a blood flow pathway 205 and a dialysate compartment having a dialysate flow pathway 210 separated by a semi-permeable membrane 215. The blood (from a patient) enters the blood flow pathway 205 via the blood inlet 130, flows through the blood flow pathway 205, and exits via the blood outlet 133. The dialysate enters the dialysate flow pathway 210 via the fluid inlet 120, flows through the dialysate flow pathway 210, and exits via the fluid outlet 125. The semi-permeable membrane 215 is configured to allow the transfer of one or more substances from the blood in the blood flow pathway 205 to the dialysate in the dialysate flow pathway 210, or visa-versa. Some examples of materials that may be used as the semipermeable membrane 215 include polymers, copolymers, metals, ceramics, composites, and/or liquid membranes. One example of a composite membrane is polysulfone-nanocrystalline cellulose composite membrane such as AN69 flat sheet membranes available from Gambro Medical. Gas-liquid contactor membranes may also be employed for transferring a substance between a liquid and gas such as for oxygenation of blood, whereby the membrane allows transfer of carbon dioxide and oxygen, such that oxygen transfers to blood from oxygen or oxygen-enriched air, and carbon dioxide transfers from the blood to the gas. Fluid membranes may also be employed. Fluid membranes comprise a lamina having through cut microchannels containing fluid and a first and second membrane support positioned to contain fluid in the microchannels.

When flowing through the dialyzer 105, the blood and the dialysate may flow in a counter-flow configuration wherein blood flows through the blood flow pathway 205 in one direction and the dialysate flows through the dialysate flow pathway 210 in the opposite direction. The dialyzer 105 is described in the context of having a counter-flow configuration although a cross-flow configuration may also be used. As the blood and water flow along the membrane 215, hemodialysis occurs. That is, waste solutes move across the semipermeable membrane 215 from the blood into the dialysate via diffusion as a result of the differential of solute concentration between the blood and the dialysate. The flow of the blood and dialysate, which may be counter-, cross- or concurrent-flow, maintains the concentration gradient of solutes between the blood and dialysate, which helps to remove more urea and creatinine from the blood. The concentrations of solutes (for example potassium, phosphorus, and urea) may be undesirably high in the blood, but low or absent in the dialysate and constant replacement of the dialysate ensures that the concentration of undesired solutes is kept low on the dialysate side of the membrane. The dialysate has levels of minerals like potassium and calcium that are similar to their natural concentration in healthy blood. For another solute, bicarbonate, the dialysate level is set at a slightly higher level than in normal blood, to encourage diffusion of bicarbonate into the blood, to maintain a patient's $CO_2$ level, and act as a pH buffer to neutralize the metabolic acidosis that is often present in these patients.

The dialyzer 105 is also configured to perform ultrafiltration wherein a pressure differential across the membrane 215 results in fluid and dissolved solutes passing across the membrane 215 from the blood to the dialysate.

The dialyzer 105 is also configured to perform hemodiafiltration wherein solute movement across the semipermeable membrane 215 is governed by convection rather than by diffusion. A positive hydrostatic pressure differential between the blood flow pathway 205 and the dialysate flow pathway 210 drives water and solutes across the semipermeable membrane 215 from the blood flow pathway to the fluid flow pathway. Solutes of both small and large molecules get dragged through the semipermeable membrane 215 along with the fluid. In a typical hemodiafiltration procedure, the direction of water and solute movement is oscillated between moving water and solutes from the blood into the dialysate and moving water and solutes from the dialysate into the blood. Over a predetermined span of time, there is a net zero loss and zero net gain of fluid from the blood into the dialysate. However, during discrete time periods within that span of time, there can be a net loss of fluid from the blood into the dialysate and a net gain of fluid into the blood from the dialysate.

Operation of Pumps to Achieve Hemodialysis without Ultrafiltration

With reference again to FIG. 1A, the dialysis system achieves hemodialysis without ultrafiltration when the flow rate through the inlet pathway 132 is equal to or substantially equal to the flow rate through the outlet pathway 137. In other words, hemodialysis without ultrafiltration is achieved where the amount of dialysate flowing into dialyzer 105 via the inlet pathway 137 is substantially equal to the amount of dialysate flowing out of the dialyzer via the outlet pathway 137 over a period time. This can be achieved by operating the first pump 135 at a first pump rate to provide a first flow rate through the inlet pathway 132 and operating the second pump 155 and the third pump 160 at respective pump rates that collectively achieve a flow rate through the outlet pathway 137 that is equal to the flow rate through the inlet pathway 132.

In an embodiment, the system performs a hemodialysis procedure utilizing all three pumps in an active state substantially continuously throughout the hemodialysis procedure. The system adjusts the pump rate of the third pump 160 to achieve a desired balance of equal flow rates between the inlet pathway 132 and the outlet pathway 137. In this embodiment, the first pump 135, second pump 155, and third pump 160 are all active throughout the hemodialysis procedure with the first and second pumps operating at different pump rates and the third pump operating at a pump rate that achieves a balanced flow rate between the inlet pathway 132 and the outlet pathway 136. The third pump is typically operated at a pump rate that is equal to the differential between the pump rate of the first pump and the pump rate of the second pump. In this manner, the second and third pumps collectively achieve a flow rate through the outlet pathway 137 that is equal to the flow rate through the inlet pathway 132.

For example, to achieve a desired flow rate of, for example, 100 ml/min through the dialyzer, the first pump 135 is set to provide a flow rate of 100 ml/min through the inlet pathway 132 and the second pump 155 is deliberately set out of balance with the first pump 135, to provide, for example, a flow rate of only 80 ml/min. This would provide a flow rate differential of 20 ml/min between the first pump and the second pump. The pump rate of third pump 160 is set to provide a flow rate of 20 ml/min, which is equal to the differential between the flow rates of the first and second pumps. In this manner, the second pump 155 and the third pump 160 collectively achieve a flow rate of 100 ml/min through the outlet pathway 137 which is equal to the flow rate of through the inlet pathway 132 such that the flow rates are balanced across the dialyzer. Under such conditions, waste solutes move across the dialyzer's semipermeable membrane from the blood stream into the dialysate via diffusion to perform hemodialysis.

The flow rates through the inlet pathway 132 and the outlet pathway 137 may be measured using one or more of the sensors S. In an embodiment, the sensors are flow rate sensors that directly measure flow rates through the inlet pathway 132 and outlet pathway 137. In another embodiment, the sensors are pressure sensors that provide indications as to the fluid pressure within the inlet pathway 132 and the fluid pressure within the outlet pathway 137. Fluid pressure is a function of the flow rate through the flow pathways and therefore provides an indirect measurement of flow rate. Where the fluid pressure in the inlet pathway 132 is equal to the fluid pressure in the outlet pathway 137, this is an indication that the flow rates are balanced between the inlet pathway and outlet pathway. Where the fluid pressure in the inlet pathway 132 is less than the fluid pressure through the outlet pathway 137, this is an indication that the flow rate through the inlet pathway 132 is less than the flow rate through the outlet pathway 137. Where the fluid pressure in the inlet pathway 132 is greater than the fluid pressure through the outlet pathway 137, this is an indication that the flow rate through the inlet pathway 132 is greater than the flow rate through the outlet pathway 137. The system of fluid pathways may include one or more damping mechanisms for dampening any extreme fluctuations in pressure within the fluid pathways.

Figure 3:
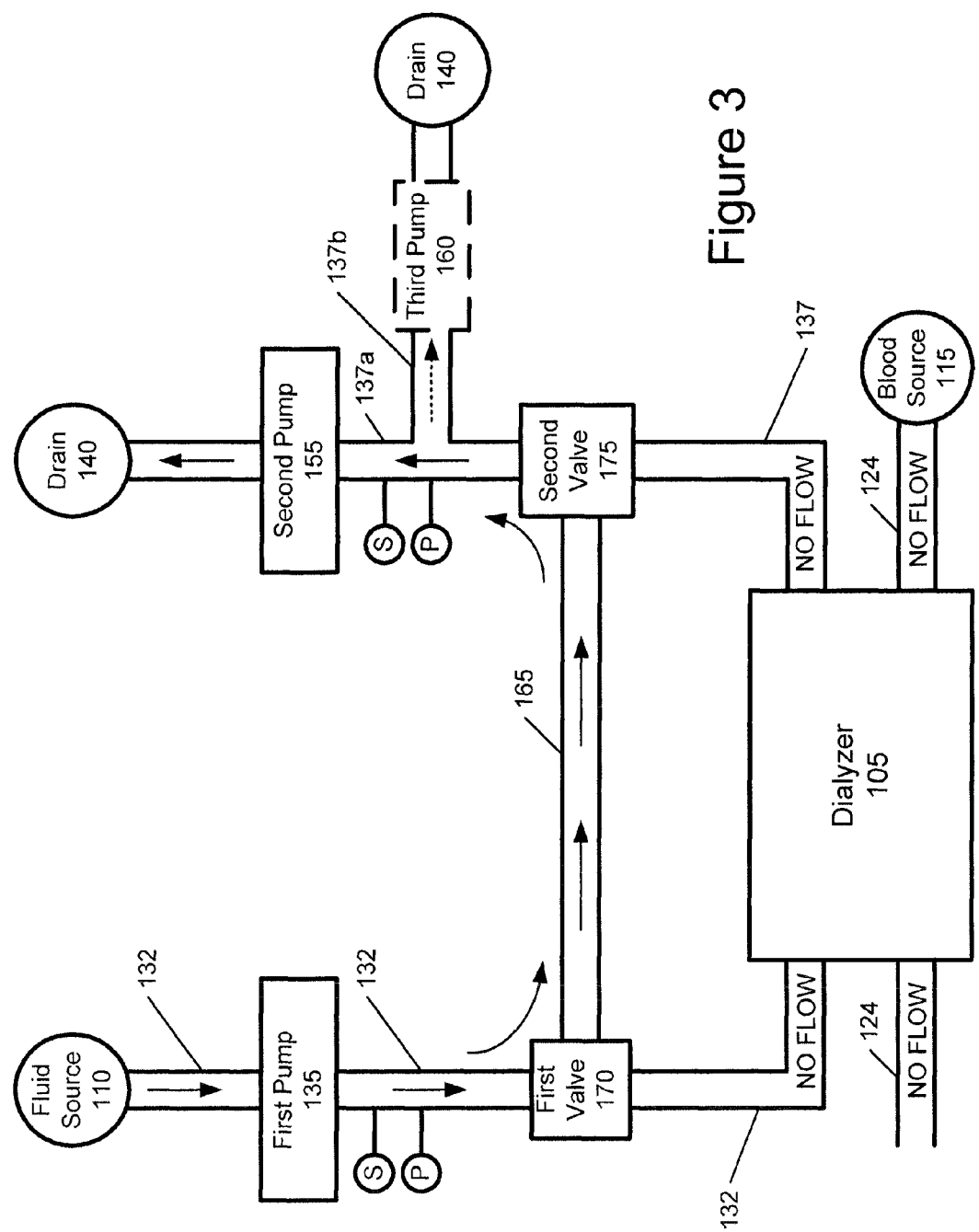
FIG. 3 shows a schematic representation of the system running in a calibration mode.

In the latter two situations, the pump rate of the third pump 160 may be adjusted in response to a pressure differential between the inlet and outlet pathways such as in a calibration procedure, to achieve a balanced flow rate between the inlet pathway 132 and outlet pathway 137. The calibration procedure may optionally be performed with the system in a calibration mode such that the first and second valves are set to cause fluid to flow through the bypass pathway 165 and bypass the dialyzer 105, as represented in FIG. 3 and described in more detail below. When the calibration procedure is performed by bypassing the dialyzer 105 and a pressure differential is detected between the inlet and outlet pathways, the flow of the third pump 160 may be appropriately adjusted 'on the fly' to increase or decrease the third pump's speed to achieve the desired flow rate in the outlet pathway 137 without having to turn the pump on or off. In this regard, the pressure sensors S and the three pumps, as well as the valves 175, may be connected in a closed loop control system to achieve automatic balancing of the flow rates.

In another embodiment, a balanced flow rate between the inlet pathway 132 and the outlet pathway 137 is achieved in theory at least by the first pump 135 and the second pump 155 operating at the same pump rate to achieve equal flow rates through the inlet pathway 132 and outlet pathway 137. Although it is theoretically possible to match the flow rates of the first pump 135 and the second pump 137, various factors may result in the actual fluid flow rate in the inlet pathway 132 differing from the actual fluid flow rate in the outlet pathway 137. The factors may include trapped air, hardware wear, and fluid leakage, which can cause the flow rates of the first and second pumps to diverge over time from a preset or desired value. Typical technologies in dialysis systems are unable to correct the flow balance for these types of factors.

Thus, there may come a time when a balanced flow rate cannot easily be achieved through use of the first and second pumps alone, and thus when there exists a need for correction to equalize the flow rates between the inlet pathway 132 and outlet pathway 137. Where the fluid flow rates are different, the third pump 160 can be used to correct the differing flow rates by being activated to pump fluid through the secondary outlet pathway 1137b at a rate that is equal to the delta between the fluid flow rate through the inlet pathway 132 and the fluid flow rate through the outlet pathway 137. The system is preferably configured such that the first pump 135 is prevented from pumping less fluid than the second pump 155 such that the first pump 135 always pumps at a higher rate than the second pump 155. The system preferably includes a control system that detects a condition where the first pump 135 inadvertently pumps at a slower rate than the second pump 155 and sets off an alarm or moves the system out of dialysis mode if such a situation occurs.

According to a flow rate correction process, the sensors S (FIG. 1) are used to measure the flow rates through the inlet pathway 132 and the outlet pathway 137. A comparison is performed between the flow rate through the inlet pathway 132 and the flow rate through the outlet pathway 137. Where the flow rates are different, the third pump 160 is activated from a de-activated state to cause fluid to flow into the secondary outlet pathway 137b at a rate selected to cause the overall flow rate in the outlet pathway 137 to be equal to the flow rate in the inlet pathway 132. A mechanism such as a servo mechanism may be used to adjust the stroke volume of the first pump 135 and/or the second pump 155 until balance of the flow rates is restored (as may be evidenced, for example, by the presence of the same fluid pressure in both the inlet pathway 132 and the outlet pathway 137).

As mentioned, the sensors S may be communicatively coupled to a control system and to the three pumps in a closed loop system. The control system includes hardware and/or software that automatically activates and/or deactivates the third pump 160 or adjusts the pump rate of the third pump 160 as needed in response to differences in detected flow rates from predetermined values or from each other, to equalize the flow rates between the inlet pathway 132 and outlet pathway 137. It should be appreciated that other measurements, such as fluid pressure in the inlet and outlet pathways, may be used to indirectly calculate the flow rates rather than directly measuring the flow rates. In this regard, the fluid pressures within the inlet pathway and the outlet pathway may be measured for any detectable change in pressure from a predetermined value or from each other. The flow pathways may be adapted to be essentially non-compliant so that a small difference in the flow rates of the first pump 135 and the second pump 155 will cause a rapid pressure change either negative or positive in magnitude.

The system may initially and/or periodically run in a calibration mode (sometimes also referred to as a UF checking mode) wherein a fluid (which may or may not be dialysate) is flowed through the flow pathways with the first valve 170 and second valve 137 set to the "bypass setting" such that fluid flowing through the system bypasses the dialyzer 105 via the bypass pathway 165. FIG. 3 shows a schematic representation of the system running in such a calibration mode where the dialyzer 105 is bypassed. In the embodiment where the system utilizes all three pumps in an active state substantially continuously throughout the hemodialysis procedure, the first and second pumps are initially deliberately set to achieve unbalanced flow rates. The sensors S in the flow pathway are then used to measure the fluid flow rate or pressure through the inlet pathway and the fluid flow rate or pressure through the outlet pathway. The third pump 160 is then set at a pump speed that achieves a substantially balanced flow rate between the inlet pathway 132 and outlet pathway 137.

In the other embodiment, the first pump 135 and second pump 155 are initially set to achieve equal flow rates without necessarily requiring the assistance of the third pump 160, which is initially inactive. The sensors S in the flow pathway are then used to measure the fluid flow rate through the inlet pathway and the fluid flow rate through the outlet pathway. Where the fluid flow rates are equal, the third pump 160 remains inactive. However, where the fluid flow rates are not equal, the third pump 160 is run at a rate that compensates for the discrepancy in flow rates between the inlet pathway 132 and outlet pathway 137. As mentioned, the third pump 160 may operate in a closed-loop relationship with the flow rate sensors and/or the pressure sensors. FIG. 3 shows the third pump 160 in phantom lines to represent the third pump may or may not be activated depending on whether there is a flow rate differential between the inlet pathway 132 and outlet pathway 137. The calibration procedure that does not require activating and de-activating the third pump is preferred as the system may run more efficiently when all three pumps are continuously operating.

After the calibration procedure is completed, the valves 170 and 175 may be set to the "dialysis setting" such that fluid flows from the source 110, through the inlet pathway 132, into the dialyzer 105, out of the dialyzer, and into the outlet pathway 137 from the dialyzer 105. When configured as such, the system can be used for dialysis by flowing dialysate into and out of the dialyzer 105 via the inlet and outlet pathways, and by also by flowing blood into and out of the dialyzer via the blood flow pathway 124. During dialysis, the previously described calibration procedure may be periodically repeated, such as at predetermined intervals, to ensure that the flow rates of the inlet and outlet pathways remain within desired ranges.

In an embodiment, calibration is run only at the beginning of a dialysis session. In a more preferred embodiment, calibration is run periodically during the dialysis session, to ensure that the desired flow balance is maintained throughout the session. The control system can cycle the valves 170 and 175 controlling incoming flow stream between the dialysis setting and the bypass setting and run the calibration steps without additional interruptions to the dialysis session. During the calibration process, when the dialysate fluid bypasses the dialyzer 105, dialysis of the blood that passes through the dialyzer during that period of time is unhampered due to no fresh dialysate being provided to the dialyzer 105, though the blood may cool slightly. As long as the calibration step can be conducted over a relatively short period of time relative to the time between calibrations, the calibration has no material effect on the quality of dialysis being provided to the patient. In an embodiment, the dialysis system can be cycled between calibration for one minute followed by 60 minutes of dialysate being delivered through the dialyzer. In another embodiment, the dialysis system can be cycled between calibration for 30 seconds followed by 120 minutes of dialysate being delivered through the dialyzer. Various different cycle times between calibration and dialysis may be chosen based on how frequently the system's calibration is to be verified and/or adjusted. If no adjustment to any of the pumps is necessary during calibration, the calibration step may be concluded in a much shorter period of time than 30-seconds, for example 5-10 seconds.

Figure 4:
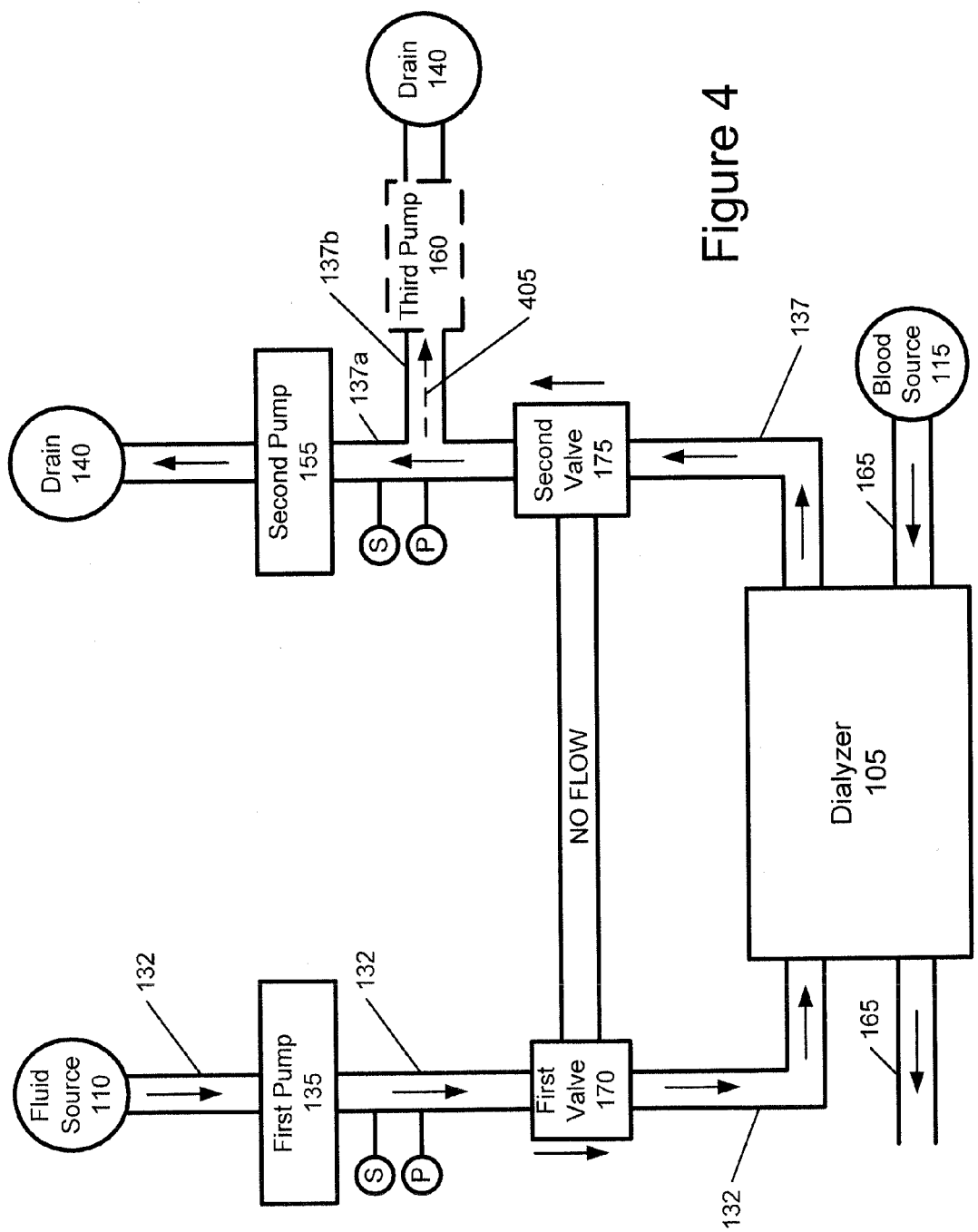
FIG. 4 shows a schematic representation of the system running in a dialysis mode.

FIG. 4 schematically shows the system running in a dialysis mode. The third pump 160 and the flow arrow 405 through the secondary outlet pathway 137b are shown in phantom lines to indicate that the third pump 160 may or may not be active while the system is in dialysis mode. The third pump 160 may be active in the situation where the third pump 160 is needed to equalize the flow rates between the inlet pathway and outlet pathways. Or, the flow rates of the inlet and outlet pathways may be equal without the assistance of the third pump 160, in which case the third pump 160 remains inactive.

Operation of Pumps to Achieve Ultrafiltration

The dialysis system achieves ultrafiltration in the situation where the flow rate through the inlet pathway 132 differs from the flow rate through the outlet pathway 137 such that there is an unbalanced flow rate across the dialyzer. Where the flow rate through the outlet pathway 137 is greater than the flow rate through the inlet pathway 132, the dialyzer 105 pulls fluid from the blood across the semipermeable membrane by a convective process in order to compensate for the unbalanced flow rate. In an embodiment, the system utilizes all three pumps substantially continuously throughout the procedure and the pump rate of the third pump 160 is adjusted to achieve a desired flow rate differential between the inlet pathway 132 and the outlet pathway 137 to perform ultrafiltration. That is, the first pump 135, second pump 155, and third pump 160 are all active with the first and second pumps operating at different pump rates. The third pump is then operated at a pump rate that intentionally achieves a desired imbalance of flow rates between the inlet pathway 132 and the outlet pathway 136 sufficient to cause ultrafiltration.

For example, to achieve the removal of fluid at a rate 10 ml/min from the blood stream, the first pump 135 is set to provide a flow rate of 100 ml/min through the inlet pathway 132 and the second pump 155 is deliberately set out of balance with the first pump 135, to provide, for example, a flow rate of only 80 ml/min. The third pump 160 is then set to provide a flow rate of 30 ml/min such that the second and third pumps collectively provide a flow rate of 110 ml/min through the outlet pathway 137. With a flow rate of 100 ml/min through the inlet pathway 132 and a flow rate of 110 ml/min through the outlet pathway, the dialyzer 105 compensates for the 10 ml/min flow rate differential by transferring 10 ml/min of fluid from the blood stream into the dialysate.

In another example, to achieve the addition of fluid at a flow rate of 10 ml/min into the blood stream, the first pump 135 is set to provide a flow rate of 100 ml/min through the inlet pathway 132 and the second pump 155 is again deliberately set out of balance with the first pump 135, to provide, for example, a flow rate of only 80 ml/min. The third pump 160 is then set to provide a flow rate of only 10 ml/min such that the second and third pumps collectively provide a flow rate of 90 ml/min through the outlet pathway 137. With a flow rate of 100 ml/min through the inlet pathway 132 and a flow rate of 90 ml/min through the outlet pathway, there is a transfer of 10 ml/min from the dialysate into the blood stream in order to compensate for the flow rate differential. It should be appreciated that the flow rate values in the preceding examples and following examples are only for purpose of example and that the actual flow rates as well as the relative flow rates can vary to achieve a desired level of ultrafiltration or reverse ultrafiltration.

The speed of the third pump 160 can be varied to selectively vary an amount of ultrafiltration. For example, if it is determined that the ultrafiltration is greater than desired when pulling fluid out of the blood, for example, the pump speed of the third pump 160 can be slowed down, reducing the amount of extra fluid that the third pump 160 draws out of the dialyzer. Where the ultrafiltration is not great enough when compared against a desired predetermined value, the pump speed of the third pump 160 may be increased in the case where fluid is being pulled out of the blood into the dialysate, for example, to draw an even greater amount of fluid out of the dialyzer and, hence, the blood.

In another embodiment, the third pump 160 may be coupled to a source of fluid such that the third pump 160 outputs extra fluid into the flow pathway via the secondary outlet pathway 137b, such as in the embodiment of FIG. 1B. The extra fluid introduced into the flow pathway is transferred across the semi-permeable membrane 215 into the blood.

Operation of Pumps to Achieve Hemodiafiltration

The dialysis system is configured to achieve hemodiafiltration by oscillating the speed of the third pump between (1) a first speed such that the second and third pump collectively achieve a flow rate through the outlet pathway that is greater than the flow rate through the inlet pathway; and (2) a second speed such that the second and third pump collectively achieve a flow rate through the outlet pathway that is less than the flow rate through the inlet pathway. In this manner, the third pump 160 can be used to intermittently alternate the flow rate differential between a state where the dialyzer 105 pulls fluid from the blood stream into the dialysate and a state where the dialyzer 105 pushes fluid from the dialysate into the blood stream. Over a predetermined span of time, there should be a zero net loss (or substantially a zero net loss) of fluid from the blood and a zero net gain (or substantially a zero net gain) of fluid into the blood for the process of hemodiafiltration. However, during that span of time, the dialyzer 105 periodically transfers fluid into the blood from the dialysate and periodically transfers fluid out of the blood into the dialysate. If ultrafiltration is desired to be performed at the same time as the hemodiafiltration, then the pumps can be operated in such a way so that in addition to the cycling of fluid into and out of the blood over time, there also occurs a net gain or loss of fluid to or from the blood over a predetermined span of time.

For example over an exemplary time span of ten minutes, the first pump 135 is set to provide a flow rate of 100 ml/min through the inlet pathway 132 and the second pump 155 is again deliberately set out of balance with the first pump 135, to provide, for example, a flow rate of only 80 ml/min. The speed of pump 160 can be cycled between a rate of 10 ml/min for a period of 30 seconds and 30 ml/min for a period of 30 seconds. During the periods when the speed of the third pump 160 is at a rate of 10 ml/min, the total flow rate through the outlet pathway 137 is 90 ml/min with the flow rate through the inlet pathway 132 at 100 ml/min, resulting in an unbalanced flow rate that causes the dialyzer 105 to transfer 10 ml/min of fluid into the blood stream. During the periods when the speed of the third pump 160 is at a rate of 30 ml/min, the total flow rate through the outlet pathway 137 is 110 ml/min with the flow rate through the inlet pathway 132 at 100 ml/min, resulting in an unbalanced flow rate that causes the dialyzer 105 to transfer 10 ml/min of fluid from the blood stream into dialysate. Over the span of ten minutes with alternating periods of 30 seconds as described above, there is a net balanced flow rate of 100 ml/min across the dialyzer without any net addition or subtraction of fluid from the blood. This serves the purpose of passing fluid to the blood across the membrane and then fluid from the blood to the dialysate across the membrane to achieve hemodiafiltration of the blood and increases the removal of large-molecular waste products that would not otherwise be effectively dialyzed. In this way, operation of the three or more-pump system can achieve all of hemodialysis, ultrafiltration and hemodiafiltration through how the speeds of the first, second, and third pumps are controlled. This type of operation has heretofore not been possible in other dialysis systems.

In another embodiment, shown in FIG. 1B, the third pump is located on the inlet flow side of the dialyzer instead of on the outlet flow path, such that the first and third pumps collectively achieve the desired inlet flow rate and the second pump achieves the desired outlet flow rate to perform one or more of hemodialysis, ultrafiltration and hemodiafiltration.

Between dialysis treatments, the flow pathways may be rinsed and/or disinfected. A rinse fluid, such as, but not limited to disinfectant solution and water, is routed through the flow pathways while the valves are in the bypass setting. During rinse mode, the third pump 160 may or may not be operated with the first pump 135 and second pump 155 to achieve fluid flow through the system.

Control of Flow Rates Using Pulsatile Pumps

In embodiments wherein the flow through flow pathways has a pulsatile nature, such as might be produced by certain types of pumps, the inherently high sensitivity of the methods described above might provide a challenge for controlling the flow rate as the small diameter and largely non-compliant flow pathways coupled with the pulsatile nature of the flow may make it difficult to measure pressures and pressure change rates sufficient to control the flow during dialysis.

In an embodiment, the pulsatile pressure signals present in a pulsatile flow configuration may be filtered out using appropriate signal conditioning. But the small volume and rigid flow pathways might cause too rapid of a pressure shift, quickly driving the pressure magnitude beyond the range of the pressure sensors. This may be particularly true for large, temporary mismatches associated with air being present in the flow pathways.

Figure 5:
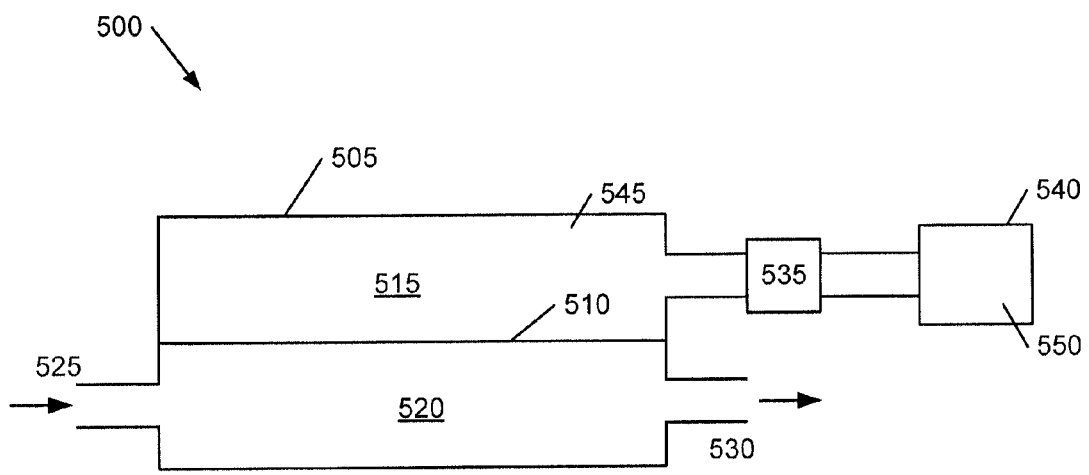
FIG. 5 is a cross-sectional view of a compliance control device.

FIG. 5 is a cross-sectional view of a compliance control device 500 that may be positioned in fluid communication with the flow pathways of the system. The device 500 is adapted to smooth out the pulsatile nature of the flow. The compliance control device 500 comprises a chamber 505 divided by a compliant diaphragm 510 defining a first chamber 515 and a second chamber 520. The first chamber 505 comprises a first chamber inlet 525 and a first chamber outlet 530 adapted for fluid communication with the flow pathways of the system. The second chamber 520 is in fluid communication with a control valve 535 and air plenum 540, wherein a non-compliant fluid 545, such as, but not limited to an inert liquid or gel, is disposed in the second chamber 520 and a compliant gas 550 is disposed in the air plenum 540.

When the dialysis system is performing hemodialysis, the control valve 535 may be closed restricting the flow of the non-compliant fluid 545 to the second chamber 520 creating a substantially non-compliant flow circuit as the compliant diaphragm 510 is restricted from complying (elastically deforming) against the now relatively rigid non-compliant fluid 545.

During calibration of the dialysis system, the control valve 535 may be opened, allowing the non-compliant fluid 545 to react with the gas 550 in the air plenum in reaction to pressure transients of the fluid in the pathway acting against the diaphragm 510. The diaphragm 510 moves in response to the pressure change and the gas 550 in the air plenum tends to moderate and smooth the pressure changes, allowing for a more precise pressure detection during calibration for flow compensation by the third pump 160.

Figure 6:
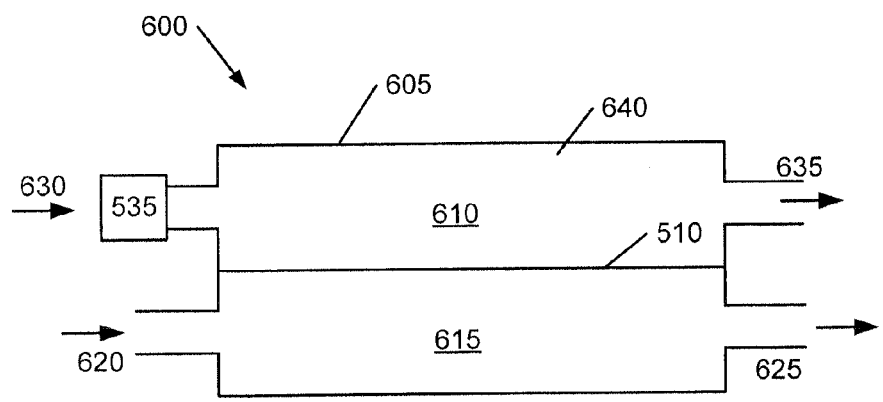
FIG. 6 is a cross-sectional view of another embodiment of a compliance control device.

FIG. 6 is a cross-sectional view of another compliance control device 600 adapted for fluid communication with the flow pathways of the system and adapted to smooth out the pulsatile nature of the flow such as during calibration. The compliance control device 600 comprises a chamber 605 divided by a compliant diaphragm 510 defining a first chamber 610 and a second chamber 615. The first chamber 610 comprises a first chamber inlet 620 and a first chamber outlet 625 adapted for fluid communication with the flow pathways of the system. The second chamber 615 comprises a second chamber inlet 630 and a second chamber outlet 635 adapted for fluid communication with a source of non-pulsatile flow of substantially non-compliant fluid 640. The fluid flow into the second chamber inlet 630 is controlled by a control valve 535 and the second chamber outlet 635 is in fluid communication with a drain.

During hemodialysis operation of the system, the control valve 535 is opened, allowing the flow of non-compliant fluid 640 to flow into the second chamber 615 and against the diaphragm 510 which restricts the movement of the diaphragm 510 and therefore creates a substantially non-compliant flow circuit. During calibration of the system, the control valve 535 is closed, restricting the flow of the non-compliant fluid 640 into the second chamber 615 with the non-compliant fluid 640 left in the second chamber 615 free to flow to the drain. Without the flow of non-compliant fluid 640 reacting against the diaphragm 510 and the remaining fluid 640 in the second chamber 615 free to drain, the fluid can react against the diaphragm 510 unconstrained by the non-compliant fluid 640. The diaphragm 510 elastically moves in response to any pressure change in the flow circuit moderating and smoothing the pressure change, allowing for a more precise pressure detection in the flow pathways for flow compensation by the third pump 160.

It is appreciated that the compliance control devices 500 and 600, such as provided in FIGS. 5 and 6, can be placed in fluid communication at any location in the flow pathways of the system such as upstream of the first valve 170 and downstream of the second valve 175, suitable for a particular purpose.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method of calibrating a dialysis system comprising a dialyzer, a dialysate inlet pump, an inlet fluid flow pathway extending from the dialysate inlet pump to the dialyzer, a dialysate outlet pump, an outlet fluid flow pathway extending from the dialyzer to the dialysate outlet pump, the dialysate outlet pump being the only pump positioned for pumping dialysate out of and away from the dialyzer through the outlet fluid flow pathway, a bypass fluid flow pathway extending from the inlet fluid flow pathway to the outlet fluid flow pathway and bypassing the dialyzer, the method comprising:
  flowing fluid from the dialysate inlet pump through the bypass fluid flow pathway to the dialysis outlet pump;
  comparing pressure of the fluid in the inlet fluid flow pathway to pressure of the fluid in the outlet fluid flow pathway;
  based on a result of the comparing step, adjusting a pump rate of the dialysate inlet pump or the dialysate outlet pump to achieve a balanced flow rate through the inlet fluid flow pathway and the outlet fluid flow pathway; and
  after the adjusting step, controlling the pump rate of the dialysate inlet pump or the dialysate outlet pump to pump fluid from the dialysate inlet pump through the inlet fluid flow pathway to the dialyzer at an inlet flow rate and through the outlet fluid flow pathway to the dialysate outlet pump from the dialyzer at an outlet flow rate different than the inlet flow rate.

2. The method of claim 1 wherein the adjusting step comprises adjusting the pump rate of the dialysate inlet pump or the dialysate outlet pump so that the pressure of the fluid in the inlet fluid flow pathway is equal to the pressure of the fluid in the outlet fluid flow pathway.

3. The method of claim 1 wherein the adjusting step comprises adjusting the pump rate such that pump rates of the dialysate inlet pump and the dialysate outlet pump are equal.

4. The method of claim 1 further comprising:
  performing the step of flowing fluid from the dialysate inlet pump through the dialyzer to the dialysate outlet pump for 60 minutes;
  after the performing step, flowing fluid from the dialysate inlet pump through the bypass fluid flow pathway to the dialysis outlet pump;
  comparing pressure of the fluid in the inlet fluid flow pathway to pressure of the fluid in the outlet fluid flow pathway;
  based on a result of the comparing step, adjusting the pump rate of the dialysate inlet pump or the dialysate outlet pump to achieve a balanced flow rate through the inlet fluid flow pathway and the outlet fluid flow pathway; and
  after the adjusting step, controlling the pump rate of the dialysate inlet pump or the dialysate outlet pump to pump fluid from the dialysate inlet pump through the inlet fluid flow pathway to the dialyzer at an inlet flow rate and through the outlet fluid flow pathway to the dialysate outlet pump from the dialyzer at an outlet flow rate different than the inlet flow rate.

5. A method of calibrating a dialysis system comprising a dialyzer, a dialysate inlet pump, an inlet fluid flow pathway extending from the dialysate inlet pump to the dialyzer, a dialysate outlet pump, an outlet fluid flow pathway extending from the dialyzer to the dialysate outlet pump, the dialysate outlet pump being the only pump positioned for pumping dialysate out of and away from the dialyzer through the outlet fluid flow pathway, a bypass fluid flow pathway extending from the inlet fluid flow pathway to the outlet fluid flow pathway and bypassing the dialyzer, the method comprising:
  flowing fluid from the dialysate inlet pump through the bypass fluid flow pathway to the dialysis outlet pump;
  sensing pressure of the flowing fluid;
  based on a result of the sensing step, adjusting a pump rate of the dialysate inlet pump or the dialysate outlet pump to achieve a balanced flow rate through the inlet fluid flow pathway and the outlet fluid flow pathway; and
  after the adjusting step, controlling the pump rate of the dialysate inlet pump or the dialysate outlet pump to pump fluid from the dialysate inlet pump through the inlet fluid flow pathway to the dialyzer at an inlet flow rate and through the outlet fluid flow pathway to the dialysate outlet pump from the dialyzer at an outlet flow rate different than the inlet flow rate.

6. The method of claim 5 wherein the adjusting step comprises adjusting the pump rate of the dialysate inlet pump or the dialysate outlet pump so that the pressure of the fluid in the inlet fluid flow pathway is equal to the pressure of the fluid in the outlet fluid flow pathway.

7. The method of claim 5 wherein the adjusting step comprises adjusting the pump rate such that pump rates of the dialysate inlet pump and the dialysate outlet pump are equal.

8. The method of claim 5 further comprising:
  performing the step of flowing fluid from the dialysate inlet pump through the dialyzer to the dialysate outlet pump for 60 minutes;
  after the performing step, flowing fluid from the dialysate inlet pump through the bypass fluid flow pathway to the dialysis outlet pump;
  sensing the pressure of the flowing fluid;
  based on a result of the sensing step, adjusting the pump rate of the dialysate inlet pump or the dialysate outlet pump to achieve a balanced flow rate through the inlet fluid flow pathway and the outlet fluid flow pathway; and
  after the adjusting step, controlling the pump rate of the dialysate inlet pump or the dialysate outlet pump to pump fluid from the dialysate inlet pump through the inlet fluid flow pathway to the dialyzer at an inlet flow rate and through the outlet fluid flow pathway to the dialysate outlet pump from the dialyzer at an outlet flow rate different than the inlet flow rate.

9. A method of calibrating a dialysis system comprising a dialyzer, a dialysate inlet pump, an inlet fluid flow pathway extending from the dialysate inlet pump to the dialyzer, a dialysate outlet pump, an outlet fluid flow pathway extending from the dialyzer to the dialysate outlet pump, a bypass fluid flow pathway extending from the inlet fluid flow pathway to the outlet fluid flow pathway and bypassing the dialyzer, and a drain, the system having no control bag between the dialyzer and the drain, the method comprising:
  flowing fluid from the dialysate inlet pump through the bypass fluid flow pathway to the dialysis outlet pump;
  sensing pressure of the flowing fluid;
  based on a result of the sensing step, adjusting a pump rate of the dialysate inlet pump or the dialysate outlet pump to achieve a balanced flow rate through the inlet fluid flow pathway and the outlet fluid flow pathway; and after the adjusting step, controlling the pump rate of the dialysate inlet pump or the dialysate outlet pump to pump fluid from the dialysate inlet pump through the inlet fluid flow pathway to the dialyzer at an inlet flow rate and through the outlet fluid flow pathway to the dialysate outlet pump from the dialyzer at an outlet flow rate different than the inlet flow rate.

10. The method of claim 9 wherein the adjusting step further comprises balancing a flow rate from the dialysate inlet pump with a flow rate of the dialysate outlet pump.

11. The method of claim 9 wherein the adjusting step comprises adjusting the pump rate of the dialysate inlet pump or the dialysate outlet pump so that the pressure of the fluid in the inlet fluid flow pathway is equal to the pressure of the fluid in the outlet fluid flow pathway.

12. The method of claim 9 wherein the adjusting step comprises adjusting the pump rate such that pump rates of the dialysate inlet pump and the dialysate outlet pump are equal.

13. The method of claim 9 further comprising:

performing the step of flowing fluid from the dialysate inlet pump through the dialyzer to the dialysate outlet pump for 60 minutes;

after the performing step, flowing fluid from the dialysate inlet pump through the bypass fluid flow pathway to the dialysis outlet pump;

comparing the pressure of the fluid in the inlet fluid flow pathway to the value of the characteristic of the fluid in the outlet fluid flow pathway;

based on a result of the comparing step, adjusting the pump rate of the dialysate inlet pump or the dialysate outlet pump to achieve a balanced flow rate through the inlet fluid flow pathway and the outlet fluid flow pathway; and after the adjusting step, controlling the pump rate of the dialysate inlet pump or the dialysate outlet pump to pump fluid from the dialysate inlet pump through the inlet fluid flow pathway at an inlet flow rate to the dialyzer and through the outlet fluid flow pathway to the dialysate outlet pump from the dialyzer at an outlet flow rate different than the inlet flow rate.

* * * * *